US006924251B1

United States Patent
Schwarz et al.

(10) Patent No.: US 6,924,251 B1
(45) Date of Patent: Aug. 2, 2005

(54) SUBSTITUTED BENZOYLCYCLOHEXANDIONES

(75) Inventors: Hans-Georg Schwarz, Langenfeld (DE); Klaus-Helmut Müller, Düsseldorf (DE); Stefan Lehr, Langenfeld (DE); Otto Schallner, Monheim (DE); Mark Wilhelm Drewes, Langenfeld (DE); Dieter Feucht, Monheim (DE); Rolf Pontzen, Leichlingen (DE); Ingo Wetcholowsky, Vinhedo (BR); Heinz-Jürgen Wroblowsky, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/743,876

(22) PCT Filed: Jul. 13, 1999

(86) PCT No.: PCT/EP99/04929

§ 371 (c)(1),
(2), (4) Date: Feb. 5, 2001

(87) PCT Pub. No.: WO00/05221

PCT Pub. Date: Feb. 3, 2000

(30) Foreign Application Priority Data

Jul. 24, 1998 (DE) .......................................... 198 33 360
May 11, 1999 (DE) .......................................... 199 21 732

(51) Int. Cl.⁷ .......................... A01N 43/54; C07D 239/04
(52) U.S. Cl. .......................... 504/242; 544/88; 544/182; 544/239; 544/298; 544/318; 544/383; 596/242; 596/243
(58) Field of Search .......................... 544/318, 88, 182, 544/239, 298, 383; 546/242, 243; 504/242; 514/269

(56) References Cited

U.S. PATENT DOCUMENTS

| | | | |
|---|---|---|---|
| 3,742,014 A | 6/1973 | Grivsky ...................... 260/465 |
| 3,978,127 A | 8/1976 | Engelhardt et al. ....... 260/570.5 |
| 4,542,127 A | 9/1985 | Hitzel et al. ................ 514/161 |
| 4,837,333 A | 6/1989 | Manley et al. .............. 548/341 |
| 5,110,343 A | 5/1992 | Ueda et al. ..................... 71/88 |
| 5,171,748 A | 12/1992 | Roberts et al. .............. 514/381 |
| 5,185,351 A | 2/1993 | Finkelstein et al. ......... 514/341 |
| 5,189,033 A | 2/1993 | Tucker ......................... 514/211 |
| 5,374,606 A | 12/1994 | Cramp et al. ................ 504/270 |
| 5,378,681 A | 1/1995 | Schallner et al. ........... 504/273 |
| 5,418,250 A | 5/1995 | Finkelstein et al. ......... 514/397 |
| 5,464,810 A | 11/1995 | Haas et al. .................. 504/273 |
| 5,476,946 A | 12/1995 | Linker et al. ................ 504/273 |
| 5,554,580 A | 9/1996 | Fischer et al. .............. 504/281 |
| 5,663,362 A | 9/1997 | Haas et al. ............... 548/263.2 |
| 5,880,147 A | 3/1999 | Yoshida et al. ............. 514/452 |
| 6,040,339 A | 3/2000 | Yoshida et al. ............. 514/452 |
| 6,063,789 A | 5/2000 | Hamley et al. ............. 514/301 |

FOREIGN PATENT DOCUMENTS

| | | |
|---|---|---|
| DE | 4405614 | 8/1995 |
| EP | 0 135 191 | 10/1988 |
| EP | 0 186 120 | 11/1988 |
| EP | 0 186 119 | 8/1989 |
| EP | 0 186 118 | 5/1990 |
| EP | 0 370 332 | 5/1990 |
| EP | 0 090 262 | 8/1992 |
| EP | 0 597 360 | 5/1994 |
| EP | 0 617 026 | 9/1994 |
| WO | 96/26200 | 8/1996 |
| WO | 97/46530 | 12/1997 |
| WO | 99/07688 | 2/1999 |

OTHER PUBLICATIONS

** Chemical Abstracts, vol. 100, No. 25, Jun. 18, 1984 Columus, Ohio, US; abstract No. 209881, Nihon Nohyaku Co. LTD.: "1,2,4–Triazolin–5–one derivatives" XP002124210 cited in the application abstract & JP 58 225070 A.
** Chemical Abstracts, vol. 113, No. 3, Jul. 16, 1990 Columbus, Ohio, US; abstract No. 23929, Murai t. et al.: "Preparation of Delta 2–1,2,4–triazolin–5–one derivatives as antiinflammatory agents" XP002124211 cited in the application abstract & JP 02 015069 A (Kaken Pharmaceutical Co., LTD.).

*Primary Examiner*—Golam M M Shameem
(74) *Attorney, Agent, or Firm*—Richard E. L. Henderson; Raymond J. Harmuth

(57) ABSTRACT

The invention relates to novel substituted benzoylcyclohexanediones of the general formula (I), (I)

in which
m, n, A, $R^1$, $R^2$, $R^3$, $R^4$ and Z are each as defined in the description,
and also to processes for their preparation and to their use as herbicides.

5 Claims, No Drawings

SUBSTITUTED BENZOYLCYCLOHEXANDIONES

This application is a 371 of PCT/EP99/04929 Jul. 13, 1999.

FIELD OF THE INVENTION

The invention relates to novel substituted benzoylcyclohexanediones, to processes for their preparation and to their use as herbicides.

BACKGROUND OF THE INVENTION

It is already known that certain substituted benzoylcyclohexanediones have herbicidal properties (cf. EP-A-090262, EP-A-135191, EP-A-186118, EP-A-186119. EP-A-186120, EP-A-319075, WO-A-96/26200, WO-A-97/46530, WO-A-99/07688). However, the activity of these compounds is not in all respects satisfactory.

SUMMARY OF THE INVENTION

This invention, accordingly, provides the novel substituted benzoylcyclohexanediones of the general formula (I),

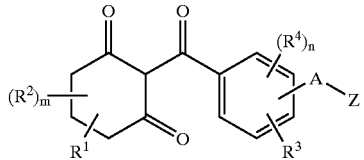

(I)

in which m represents the numbers 0, 1, 2 or 3, n represents the numbers 0, 1, 2 or 3, A represents the single bond or represents alkanediyl (alkylene).

$R^1$ represents hydrogen or represents in each case optionally substituted alkyl or alkoxycarbonyl, $R^2$ represents optionally substituted alkyl, or together with $R^1$ represents alkanediyl (alkylene) where in this case m represents 1 and $R^1$ and $R^2$ are located at the same carbon atom ("geminal") or at two adjacent carbon atoms ("vicinal"), $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylamino-sulphonyl, and Z represents an optionally substituted 4- to 12-membered, saturated or unsaturated, monocyclic or bicyclic, heterocyclic grouping which contains 1 to 4 heteroatoms (up to 4 nitrogen atoms and, if appropriate, —alternatively or additionally—one oxygen atom or one sulphur atom, or one SO grouping or one $SO_2$ grouping), and which additionally contains one to three oxo groups (C=O) and/or thioxo groups (C=S) as components of the heterocycle, including all possible tautomeric forms of the compounds of the general formula (I) and the possible salts of the compounds of the general formula (I).

In the definitions, the hydrocarbon chains, such as alkyl or alkanediyl are in each case straight-chain or branched—including in combination with heteroatoms, such as in alkoxy.

In addition to the compounds of the general formula (I)—above—it is in each case also possible for the corresponding tautomeric forms—shown in exemplary manner below—to be present.

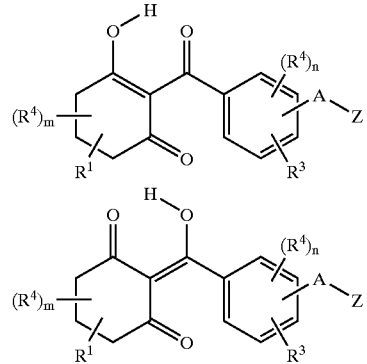

Preferred substituents of the radicals listed in the formula shown above are illustrated below:

m preferably represents the numbers 0, 1 or 2.

n preferably represents the numbers 0, 1 or 2.

A preferably represents a single bond or represents alkanediyl (alkylene) having 1 to 4 carbon atoms.

$R^1$ preferably represents hydrogen, represents optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms or represents alkoxycarbonyl having up to 6 carbon atoms.

$R^2$ preferably represents optionally halogen-substituted alkyl having 1 to 6 carbon atoms, or together with $R^1$ represents alkanediyl (alkylene) having 2 to 5 carbon atoms, where in this case m represents 1 and $R^1$ and $R^2$ are located at the same carbon atom ("geminal") or at two adjacent carbon atoms ("vicinal").

$R^3$ preferably represents hydrogen, nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups.

$R^4$ preferably represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups.

Z preferably represents one of the heterocyclic groupings below

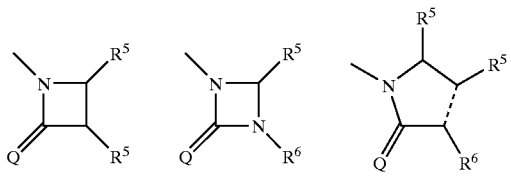

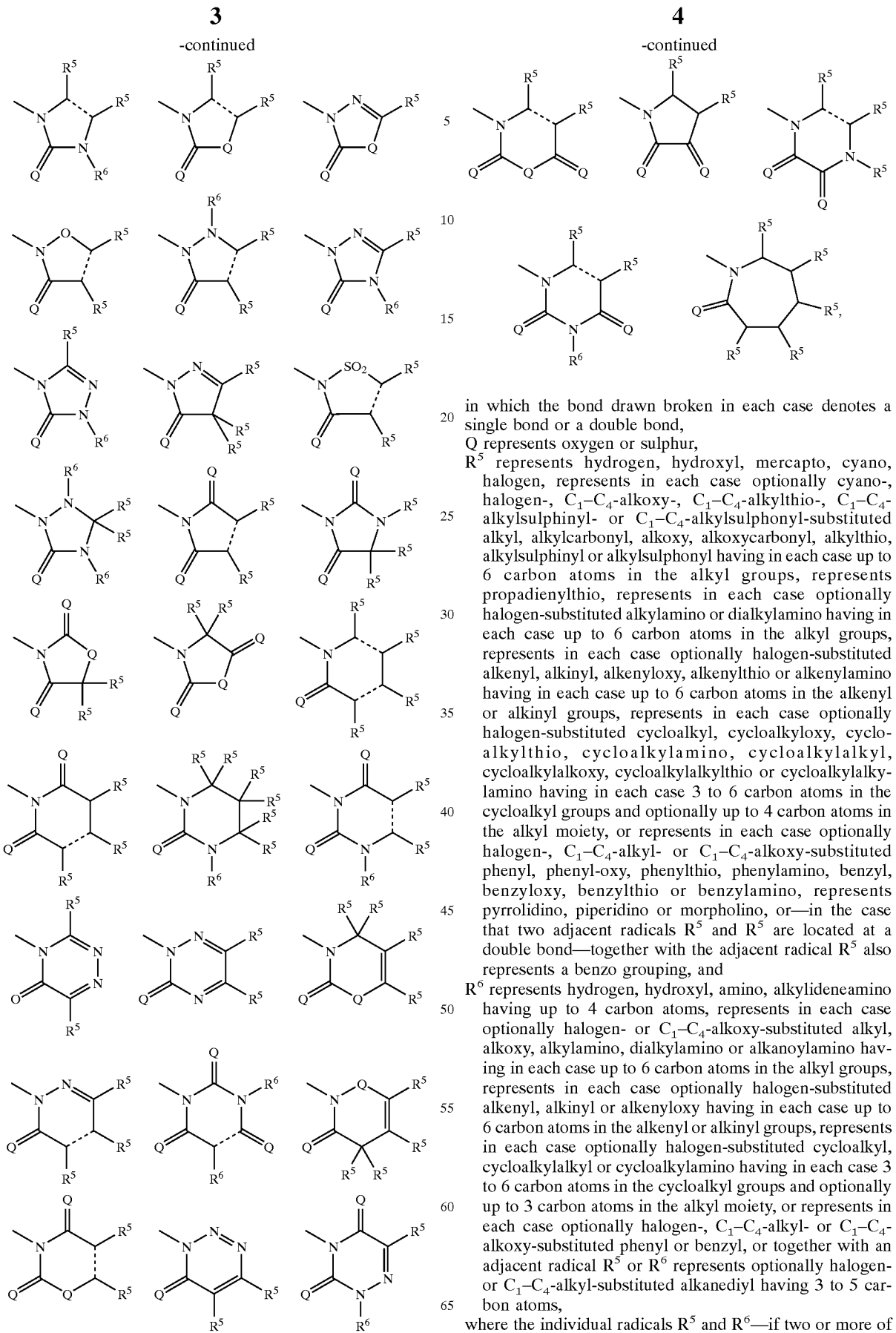

in which the bond drawn broken in each case denotes a single bond or a double bond, Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents propadienylthio, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyl-oxy, phenylthio, phenylamino, benzyl, benzyloxy, benzylthio or benzylamino, represents pyrrolidino, piperidino or morpholino, or—in the case that two adjacent radicals $R^5$ and $R^5$ are located at a double bond—together with the adjacent radical $R^5$ also represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if two or more of them are attached to the same heterocyclic groupings, may have identical or different meanings in the context of the above definition.

A particularly preferably represents a single bond, methylene, ethylidene (ethane-1,1-diyl) or dimethylene (ethane-1,2-diyl).

$R^1$ particularly preferably represents hydrogen, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i- or s-butyl, or represents methoxycarbonyl, ethoxycarbonyl, n- or i-propoxycarbonyl.

$R^2$ particularly preferably represents methyl, ethyl, n- or i-propyl, or together with $R^1$ represents methylene, ethane-1,1-diyl (ethylidene, —CH(CH$_3$)—), ethane-1,2-diyl (dimethylene, —CH$_2$CH$_2$—), propane-1,3-diyl (trimethylene, —CH$_2$CH$_2$CH$_2$—), butane-1,4-diyl (tetramethylene, —CH$_2$CH$_2$CH$_2$CH$_2$—) or pentane-1,5-diyl (pentamethylene, —CH$_2$CH$_2$CH$_2$CH$_2$CH$_2$—), where in this case m represents 1 and $R^1$ and $R^2$ are located at the same carbon atom ("geminal") or at two adjacent carbon atoms ("vicinal").

$R^3$ particularly preferably represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine-and/or; chlorine-substituted methylthio, ethylthio, n- or i-propylthio, methyl-sulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylamino-sulphonyl or diethylamino-sulphonyl.

$R^4$ particularly preferably represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl-or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylamino-sulphonyl.

Z particularly preferably represents the heterocyclic grouping below

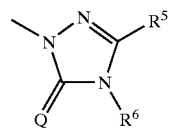

$R^5$ particularly preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-1-propylamino, represents in each case optionally fluorine- and/or chlorine-substituted ethenyl, propenyl, butenenyl, ethinyl, propinyl, butinyl, propenyloxy, butenyloxy, propenylthio, butenylthio, propenylamino or butenylamino, represents in each case optionally fluorine-and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropyl-amino, cyclobutylamino, cyclopentylamino, cyclohexylamino, cyclopropyl-methyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, or—in the case that two adjacent radicals $R^5$ and $R^5$ are located at a double bond—together with the adjacent radical $R^5$ also represents a benzo grouping, $R^6$ particularly preferably represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine-and/or chlorine-substituted cyclopropyl, cyclobutyl, cyclopentyl, cyclohexyl, cyclopropylmethyl, cyclobutylmethyl, cyclopentylmethyl or cyclohexyl-methyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene), butane-1,4-diyl (tetramethylene) or pentane-1,5-diyl (pentamethylene), where the individual radicals $R^5$ and $R^6$—if two or more of them are attached to the same heterocyclic groupings, may have identical or different meanings in the context of the above definition.

A very particularly preferably represents a single bond or represents methylene.

$R^1$ very particularly preferably represents hydrogen, methyl, ethyl, n- or i-propyl.

$R^2$ very particularly preferably represents methyl.

$R^3$ very particularly preferably represents hydrogen, nitro, cyano, fluorine, chlorine, bromine, iodine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methyl-sulphinyl, ethylsulphinyl, methylsulphonyl, ethylsulphonyl or dimethylaminosulphonyl.

$R^4$ very particularly preferably represents nitro, cyano, fluorine, chlorine, bromine, methyl, ethyl, trifluoromethyl, methoxymethyl, methylthiomethyl, methylsulphinylmethyl, methylsulphonylmethyl, methoxy, ethoxy, difluoro-methoxy, trifluoromethoxy, methylthio, ethylthio, methylsulphinyl, ethyl-sulphinyl, methylsulphonyl, ethylsulphonyl or dimethylaminosulphonyl.

$R^5$ very particularly preferably represents hydrogen, hydroxyl, chlorine, bromine, methyl, ethyl, n- or i-propyl, n-, i-, s- or t-butyl, difluoromethyl, dichloro-methyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-1-propyl, chloro-n-propyl, chloro-1-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloro-ethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulphinyl, ethylsulphinyl, n- or i-propylsulphinyl, methylsulphonyl, ethylsulphonyl, n- or i-propylsulphonyl, dimethylamino, propenylthio, butenylthio, propinylthio, butinylthio, cyclopropyl, cyclopropylmethyl, cyclopropylmethoxy, phenyl or phenoxy.

$R^6$ very particularly preferably represents amino, methyl, ethyl, n- or i-propyl, n-, i-, s- or t-butyl, methoxy, ethoxy, methylamino, dimethylamino, cycloproypyl or cyclopropylmethyl, or together with $R^5$ represents propane-1,3-diyl (trimethylene), butane-1,4-diyl (tetramethylene) or pentane-1,5-diyl (penta-methylene).

A most preferably represents methylene.

The invention preferably provides the sodium, potassium, magnesium, calcium, ammonium, $C_1$–$C_4$-alkyl-ammonium-, di-($C_1$–$C_4$-alkyl)-ammonium-, tri-($C_1$–$C_4$-alkyl)-ammonium-, tetra-($C_1$–$C_4$-alkyl)-ammonium, tri-($C_1$–$C_4$-alkyl)-sulphonium. $C_5$- or $C_6$-cycloalkyl-ammonium and di-($C_1$–$C_2$-alkyl)-benzyl-ammonium salts of the compounds of the formula (I), in which m, n, A, $R^1$, $R^2$, $R^3$, $R^4$ and Z are each as defined above.

Preference according to the invention is given to compounds of the formula (I) which contain a combination of the meanings mentioned above as being preferred.

Particular preference according to the invention is given to compounds of the formula (I) which contain a combination of the meanings listed above as being particularly preferred.

Very particular preference according to the invention is given to the compounds of the formula (I) which contain a combination of the meanings listed above as being very particularly preferred.

Compounds of the general formulae (IA), (IB) and (IC) below are particularly emphasized as being according to the invention:

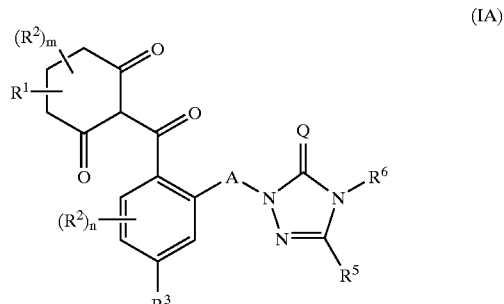

(IA)

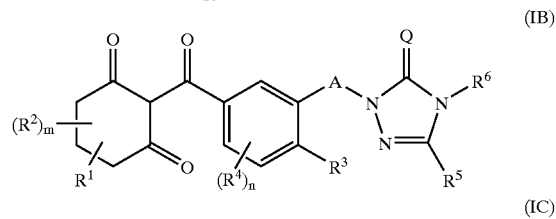

(IB)

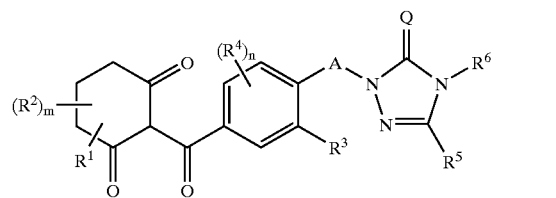

(IC)

in which
m represents the numbers 0, 1 or 2,
n represents the numbers 0, 1 or 2,
A particularly preferably represents a single bond or represents methylene,
Q represents oxygen or sulphur,
$R^1$ represents hydrogen, methyl, ethyl, n- or i-propyl,
$R^2$ represents methyl,
$R^3$ represents hydrogen, nitro, cyano, fluorine, chlorine, bromine, iodine, methyl. ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.
$R^4$ represents nitro, cyano, fluorine, chlorine, bromine, methyl, ethyl, trifluoromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl,
$R^5$ represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-1-propyl, chloro-n-propyl, chloro-1-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulphinyl, ethylsulphinyl, n- or i-propylsulphinyl, methylsulphonyl, ethylsulphonyl, n- or i-propylsulphonyl, dimethylamino, propenylthio, butenylthio, propinylthio, butinylthio, cyclopropyl, cyclopropylmethyl, cyclopropylmethoxy, phenyl or phenoxy, and $R^6$ represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl (trimethylene), butane-1,4-diyl (tetramethylene) or pentane-1,5-diyl (pentamethylene).

Here, very particular emphasis is given to the compounds of the formula (IA) in which A represents methylene.

The abovementioned general or preferred radical definitions apply both to the end products of the formula (I) and also, correspondingly, to the starting materials or intermediates required in each case for the preparation. These radical definitions can be combined with one another at will, i.e. including combinations between the given preferred ranges.

Examples of compounds of the general formula (I) according to the invention are listed in the groups below.

Group 1

(IA-1)

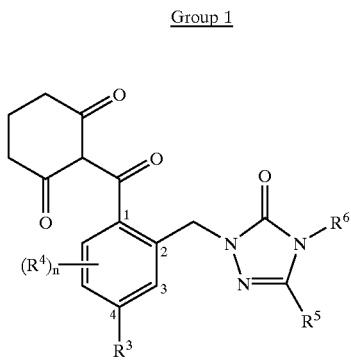

Here, $R^3$, $(R^4)_n$, $R^5$ and $R^6$ each have, for example, the meanings given in the table below:

| $R^3$ | (position-) $(R^4)_n$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |
| I | — | $CF_3$ | $CH_3$ |
| $NO_2$ | — | $CF_3$ | $CH_3$ |
| CN | — | $CF_3$ | $CH_3$ |
| $CH_3$ | — | $CF_3$ | $CH_3$ |
| $OCH_3$ | — | $CF_3$ | $CH_3$ |
| $CF_3$ | — | $CF_3$ | $CH_3$ |
| $OCHF_2$ | — | $CF_3$ | $CH_3$ |
| $OCF_3$ | — | $CF_3$ | $CH_3$ |
| $SO_2CH_3$ | — | $CF_3$ | $CH_3$ |
| H | — | $OCH_3$ | $CH_3$ |

-continued

| $R^3$ | (position-) $(R^4)_n$ | $R^5$ | $R^6$ |
|---|---|---|---|
| F | — | $OCH_3$ | $CH_3$ |
| Cl | — | $OCH_3$ | $CH_3$ |
| Br | — | $OCH_3$ | $CH_3$ |
| I | — | $OCH_3$ | $CH_3$ |
| $NO_2$ | — | $OCH_3$ | $CH_3$ |
| CN | — | $OCH_3$ | $CH_3$ |
| $CH_3$ | — | $OCH_3$ | $CH_3$ |
| $OCH_3$ | — | $OCH_3$ | $CH_3$ |
| $CF_3$ | — | $OCH_3$ | $CH_3$ |
| $OCHF_2$ | — | $OCH_3$ | $CH_3$ |
| $OCF_3$ | — | $OCH_3$ | $CH_3$ |
| $SO_2CH_3$ | — | $OCH_3$ | $CH_3$ |
| H | — | $SCH_3$ | $CH_3$ |
| F | — | $SCH_3$ | $CH_3$ |
| Cl | — | $SCH_3$ | $CH_3$ |
| Br | — | $SCH_3$ | $CH_3$ |
| I | — | $SCH_3$ | $CH_3$ |
| $NO_2$ | — | $SCH_3$ | $CH_3$ |
| CN | — | $SCH_3$ | $CH_3$ |
| $CH_3$ | — | $SCH_3$ | $CH_3$ |
| $OCH_3$ | — | $SCH_3$ | $CH_3$ |
| $CF_3$ | — | $SCH_3$ | $CH_3$ |
| $OCHF_2$ | — | $SCH_3$ | $CH_3$ |
| $OCF_3$ | — | $SCH_3$ | $CH_3$ |
| $SO_2CH_3$ | — | $SCH_3$ | $CH_3$ |
| H | — | $OC_2H_5$ | $CH_3$ |
| F | — | $OC_2H_5$ | $CH_3$ |
| Cl | — | $OC_2H_5$ | $CH_3$ |
| Br | — | $OC_2H_5$ | $CH_3$ |
| I | — | $OC_2H_5$ | $CH_3$ |
| $NO_2$ | — | $OC_2H_5$ | $CH_3$ |
| CN | — | $OC_2H_5$ | $CH_3$ |
| $CH_3$ | — | $OC_2H_5$ | $CH_3$ |
| $OCH_3$ | — | $OC_2H_5$ | $CH_3$ |
| $CF_3$ | — | $OC_2H_5$ | $CH_3$ |
| $OCHF_2$ | — | $OC_2H_5$ | $CH_3$ |
| $OCF_3$ | — | $OC_2H_5$ | $CH_3$ |
| $SO_2CH_3$ | — | $OC_2H_5$ | $CH_3$ |
| H | — | $N(CH_3)_2$ | $CH_3$ |
| F | — | $N(CH_3)_2$ | $CH_3$ |
| Cl | — | $N(CH_3)_2$ | $CH_3$ |
| Br | — | $N(CH_3)_2$ | $CH_3$ |
| I | — | $N(CH_3)_2$ | $CH_3$ |
| $NO_2$ | — | $N(CH_3)_2$ | $CH_3$ |
| CN | — | $N(CH_3)_2$ | $CH_3$ |
| $CH_3$ | — | $N(CH_3)_2$ | $CH_3$ |
| $OCH_3$ | — | $N(CH_3)_2$ | $CH_3$ |
| $CF_3$ | — | $N(CH_3)_2$ | $CH_3$ |
| $OCHF_2$ | — | $N(CH_3)_2$ | $CH_3$ |
| $OCF_3$ | — | $N(CH_3)_2$ | $CH_3$ |
| $SO_2CH_3$ | — | $N(CH_3)_2$ | $CH_3$ |
| H | — | $OCH_3$ | cyclopropyl |
| F | — | $OCH_3$ | cyclopropyl |
| Cl | — | $OCH_3$ | cyclopropyl |
| Br | — | $OCH_3$ | cyclopropyl |
| I | — | $OCH_3$ | cyclopropyl |
| $NO_2$ | — | $OCH_3$ | cyclopropyl |

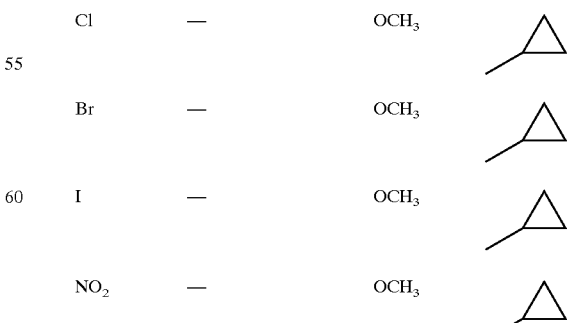

-continued

| R³ | (position-) (R⁴)ₙ | R⁵ | R⁶ |
|---|---|---|---|
| CN | — | OCH₃ |  |
| CH₃ | — | OCH₃ |  |
| OCH₃ | — | OCH₃ |  |
| CF₃ | — | OCH₃ |  |
| OCHF₂ | — | OCH₃ |  |
| OCF₃ | — | OCH₃ |  |
| SO₂CH₃ | — | OCH₃ |  |
| H | (3-) Cl | CF₃ | CH₃ |
| F | (3-) Cl | CH₃ | CH₃ |
| Cl | (3-) Cl | OCH₃ | CH₃ |
| Br | (3-) Cl | Br |  |
| Cl | (3-) Cl | CF₃ | CH₃ |
| NO₂ | (3-) Cl | CH₃ | CH₃ |
| Cl | (3-) Cl | SCH₃ | CH₃ |
| CH₃ | (3-) Cl | Cl | CH₃ |
| OCH₃ | (3-) Cl | OCH₃ | CH₃ |
| CF₃ | (3-) Cl | CF₃ | CH₃ |
| OCHF₂ | (3-) Cl | CH₃ | CH₃ |
| OCF₃ | (3-) Cl | CH₃ | CH₃ |
| SO₂CH₃ | (3-) Cl | OCH₃ | CH₃ |

Group 2

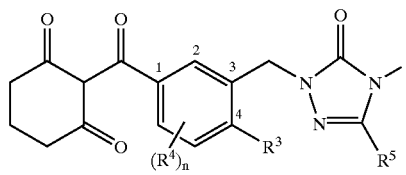

(IB-1)

Here R³, (R⁴)ₙ, R⁵ and R⁶ each have, for example, the meanings given in the table below:

| R³ | (position-) (R⁴)ₙ | R⁵ | R⁶ |
|---|---|---|---|
| Cl | (2-) Cl | CF₃ | CH₃ |
| Cl | (2-) Cl | SCH₃ | CH₃ |
| Cl | (2-) Cl | SC₂H₅ | CH₃ |
| Cl | (2-) Cl | SC₃H₇ | CH₃ |
| Cl | (2-) Cl | SC₃H₇-i | CH₃ |
| Cl | (2-) Cl |  | CH₃ |
| Cl | (2-) Cl |  | CH₃ |
| Cl | (2-) Cl |  | CH₃ |
| Cl | (2-) Cl |  | CH₃ |
| Cl | (2-) Cl |  | CH₃ |
| Cl | (2-) Cl |  | CH₃ |
| Cl | (2-) Cl | SCH=C=CH₂ | CH₃ |
| Cl | (2-) Cl | SCH₂CN | CH₃ |
| Cl | (2-) Cl | SCH₂CH₂CN | CH₃ |
| Cl | (2-) Cl | OCH₃ | CH₃ |
| Cl | (2-) Cl | OC₂H₅ | CH₃ |
| Cl | (2-) Cl | OC₃H₇ | CH₃ |
| Cl | (2-) Cl | OC₃H₇-i | CH₃ |
| Cl | (2-) Cl | OC₄H₉ | CH₃ |
| Cl | (2-) Cl | OCH₂CF₃ | CH₃ |
| Cl | (2-) Cl |  | CH₃ |
| Cl | (2-) Cl | OC₆H₅ | CH₃ |
| Cl | (2-) Cl | H | CH₃ |
| Cl | (2-) Cl | CH₃ | CH₃ |
| Cl | (2-) Cl | C₂H₅ | CH₃ |
| Cl | (2-) Cl | C₃H₇ | CH₃ |
| Cl | (2-) Cl | C₃H₇-i | CH₃ |
| Cl | (2-) Cl | C₄H₉ | CH₃ |
| Cl | (2-) Cl | C₄H₉-i | CH₃ |
| Cl | (2-) Cl | C₄H₉-s | CH₃ |
| Cl | (2-) Cl | C₄H₉-t | CH₃ |
| Cl | (2-) Cl |  | CH₃ |
| Cl | (2-) Cl |  | CH₃ |
| Cl | (2-) Cl | CH=CHCH₃ | CH₃ |
| Cl | (2-) Cl |  | CH₃ |

-continued

| $R^3$ | (position-) $(R^4)_n$ | $R^5$ | $R^6$ |
|---|---|---|---|
| Cl | (2-) Cl | 4-chlorophenyl | $CH_3$ |
| Cl | (2-) Cl | phenylethyl | $CH_3$ |
| Cl | (2-) Cl | $N(CH_3)_2$ | $CH_3$ |
| Cl | (2-) Cl | N-methylmorpholinyl | $CH_3$ |
| Cl | (2-) Cl | Cl | $CH_3$ |
| Cl | (2-) Cl | Br | $CH_3$ |
| $SO_2CH_3$ | (2-) Cl | $CF_3$ | $CH_3$ |
| $SO_2CH_3$ | (2-) Cl | $SCH_3$ | $CH_3$ |
| $SO_2CH_3$ | (2-) Cl | $SC_2H_5$ | $CH_3$ |
| $SO_2CH_3$ | (2-) Cl | $SC_3H_7$ | $CH_3$ |
| $SO_2CH_3$ | (2-) Cl | $SC_3H_7$-i | $CH_3$ |
| $SO_2CH_3$ | (2-) Cl | $SCH_2CH=CH_2$ | $CH_3$ |
| $SO_2CH_3$ | (2-) Cl | $SCH_2C{\equiv}CH$ | $CH_3$ |
| $SO_2CH_3$ | (2-) Cl | $SCH=CHCH_3$ | $CH_3$ |
| $SO_2CH_3$ | (2-) Cl | $SC{\equiv}CH$ | $CH_3$ |
| $SO_2CH_3$ | (2-) Cl | $SCH_2$-cyclopropyl | $CH_3$ |
| $SO_2CH_3$ | (2-) Cl | $SCH{=}C{=}CH_2$ | $CH_3$ |
| $SO_2CH_3$ | (2-) Cl | $SCH_2CN$ | $CH_3$ |
| $SO_2CH_3$ | (2-) Cl | $SCH_2CH_2CN$ | $CH_3$ |
| $SO_2CH_3$ | (2-) Cl | $OCH_3$ | $CH_3$ |
| $SO_2CH_3$ | (2-) Cl | $OC_2H_5$ | $CH_3$ |
| $SO_2CH_3$ | (2-) Cl | $OC_3H_7$ | $CH_3$ |
| $SO_2CH_3$ | (2-) Cl | $OC_3H_7$-i | $CH_3$ |
| $SO_2CH_3$ | (2-) Cl | $OC_4H_9$ | $CH_3$ |
| $SO_2CH_3$ | (2-) Cl | $OCH_2CF_3$ | $CH_3$ |
| $SO_2CH_3$ | (2-) Cl | $OCH_2$-cyclopropyl | $CH_3$ |
| $SO_2CH_3$ | (2-) Cl | $OC_6H_5$ | $CH_3$ |
| $SO_2CH_3$ | (2-) Cl | H | $CH_3$ |
| $SO_2CH_3$ | (2-) Cl | $CH_3$ | $CH_3$ |
| $SO_2CH_3$ | (2-) Cl | $C_2H_5$ | $CH_3$ |
| $SO_2CH_3$ | (2-) Cl | $C_3H_7$ | $CH_3$ |
| $SO_2CH_3$ | (2-) Cl | $C_3H_7$-i | $CH_3$ |
| $SO_2CH_3$ | (2-) Cl | $C_4H_9$ | $CH_3$ |
| $SO_2CH_3$ | (2-) Cl | $C_4H_9$-i | $CH_3$ |
| $SO_2CH_3$ | (2-) Cl | $C_4H_9$-s | $CH_3$ |
| $SO_2CH_3$ | (2-) Cl | $C_4H_9$-t | $CH_3$ |
| $SO_2CH_3$ | (2-) Cl | cyclopropyl | $CH_3$ |
| $SO_2CH_3$ | (2-) Cl | cyclopropylmethyl | $CH_3$ |
| $SO_2CH_3$ | (2-) Cl | $CH{=}CHCH_3$ | $CH_3$ |
| $SO_2CH_3$ | (2-) Cl | phenyl | $CH_3$ |
| $SO_2CH_3$ | (2-) Cl | 4-chlorophenyl | $CH_3$ |
| $SO_2CH_3$ | (2-) Cl | phenylethyl | $CH_3$ |
| $SO_2CH_3$ | (2-) Cl | $N(CH_3)_2$ | $CH_3$ |
| $SO_2CH_3$ | (2-) Cl | N-methylmorpholinyl | $CH_3$ |
| $SO_2CH_3$ | (2-) Cl | Cl | $CH_3$ |
| $SO_2CH_3$ | (2-) Cl | Br | $CH_3$ |
| Cl | (2-) $SO_2CH_3$ | $CF_3$ | $CH_3$ |
| Cl | (2-) $SO_2CH_3$ | $SCH_3$ | $CH_3$ |
| Cl | (2-) $SO_2CH_3$ | $SC_2H_5$ | $CH_3$ |
| Cl | (2-) $SO_2CH_3$ | $SC_3H_7$ | $CH_3$ |
| Cl | (2-) $SO_2CH_3$ | $SC_3H_7$-i | $CH_3$ |
| Cl | (2-) $SO_2CH_3$ | $SCH_2CH=CH_2$ | $CH_3$ |
| Cl | (2-) $SO_2CH_3$ | $SCH_2C{\equiv}CH$ | $CH_3$ |
| Cl | (2-) $SO_2CH_3$ | $SCH=CHCH_3$ | $CH_3$ |
| Cl | (2-) $SO_2CH_3$ | $SC{\equiv}CH$ | $CH_3$ |

-continued

| R³ | (position-) (R⁴)ₙ | R⁵ | R⁶ |
|---|---|---|---|
| Cl | (2-) SO₂CH₃ |  | CH₃ |
| Cl | (2-) SO₂CH₃ | SCH=C=CH₂ | CH₃ |
| Cl | (2-) SO₂CH₃ | SCH₂CN | CH₃ |
| Cl | (2-) SO₂CH₃ | SCH₂CH₂CN | CH₃ |
| Cl | (2-) SO₂CH₃ | OCH₃ | CH₃ |
| Cl | (2-) SO₂CH₃ | OC₂H₅ | CH₃ |
| Cl | (2-) SO₂CH₃ | OC₃H₇ | CH₃ |
| Cl | (2-) SO₂CH₃ | OC₃H₇-i | CH₃ |
| Cl | (2-) SO₂CH₃ | OC₄H₉ | CH₃ |
| Cl | (2-) SO₂CH₃ | OCH₂CF₃ | CH₃ |
| Cl | (2-) SO₂CH₃ |  | CH₃ |
| Cl | (2-) SO₂CH₃ | OC₆H₅ | CH₃ |
| Cl | (2-) SO₂CH₃ | H | CH₃ |
| Cl | (2-) SO₂CH₃ | CH₃ | CH₃ |
| Cl | (2-) SO₂CH₃ | C₂H₅ | CH₃ |
| Cl | (2-) SO₂CH₃ | C₃H₇ | CH₃ |
| Cl | (2-) SO₂CH₃ | C₃H₇-i | CH₃ |
| Cl | (2-) SO₂CH₃ | C₄H₉ | CH₃ |
| Cl | (2-) SO₂CH₃ | C₄H₉-i | CH₃ |
| Cl | (2-) SO₂CH₃ | C₄H₉-s | CH₃ |
| Cl | (2-) SO₂CH₃ | C₄H₉-t | CH₃ |
| Cl | (2-) SO₂CH₃ |  | CH₃ |
| Cl | (2-) SO₂CH₃ | 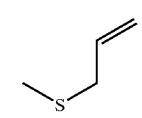 | CH₃ |
| Cl | (2-) SO₂CH₃ | CH=CHCH₃ | CH₃ |
| Cl | (2-) SO₂CH₃ |  | CH₃ |
| Cl | (2-) SO₂CH₃ | 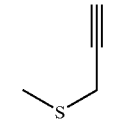 | CH₃ |
| Cl | (2-) SO₂CH₃ |  | CH₃ |
| Cl | (2-) SO₂CH₃ | N(CH₃)₂ | CH₃ |
| Cl | (2-) SO₂CH₃ | 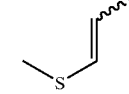 | CH₃ |
| Cl | (2-) SO₂CH₃ | Cl | CH₃ |
| Cl | (2-) SO₂CH₃ | Br | CH₃ |
| Cl | (2-) Cl | CF₃ |  |
| Cl | (2-) Cl | SCH₃ | 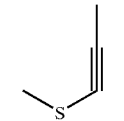 |
| Cl | (2-) Cl | SC₂H₅ |  |
| Cl | (2-) Cl | SC₃H₇ | 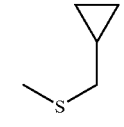 |
| Cl | (2-) Cl | SC₃H₇-i |  |
| Cl | (2-) Cl |  |  |
| Cl | (2-) Cl |  |  |
| Cl | (2-) Cl |  |  |
| Cl | (2-) Cl |  |  |
| Cl | (2-) Cl |  |  |
| Cl | (2-) Cl | SCH=C=CH₂ |  |
| Cl | (2-) Cl | SCH₂CN |  |
| Cl | (2-) Cl | SCH₂CH₂CN |  |
| Cl | (2-) Cl | OCH₃ |  |
| Cl | (2-) Cl | OC₂H₅ |  |
| Cl | (2-) Cl | OC₃H₇ |  |

-continued

| R³ | (position-)(R⁴)ₙ | R⁵ | R⁶ |
|---|---|---|---|
| Cl | (2-) Cl | OC₃H₇-i |  |
| Cl | (2-) Cl | OC₄H₉ |  |
| Cl | (2-) Cl | OCH₂CF₃ |  |
| Cl | (2-) Cl | 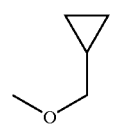 |  |
| Cl | (2-) Cl | OC₆H₅ |  |
| Cl | (2-) Cl | H |  |
| Cl | (2-) Cl | CH₃ |  |
| Cl | (2-) Cl | C₂H₅ |  |
| Cl | (2-) Cl | C₃H₇ |  |
| Cl | (2-) Cl | C₃H₇-i |  |
| Cl | (2-) Cl | C₄H₉ |  |
| Cl | (2-) Cl | C₄H₉-i |  |
| Cl | (2-) Cl | C₄H₉-s |  |
| Cl | (2-) Cl | C₄H₉-t |  |
| Cl | (2-) Cl |  |  |
| Cl | (2-) Cl |  | 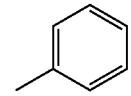 |
| Cl | (2-) Cl | CH=CHCH₃ | 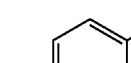 |

-continued

| R³ | (position-)(R⁴)ₙ | R⁵ | R⁶ |
|---|---|---|---|
| Cl | (2-) Cl | 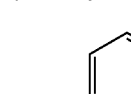 | 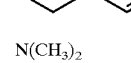 |
| Cl | (2-) Cl | 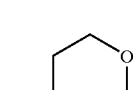 | 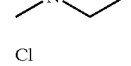 |
| Cl | (2-) Cl |  | 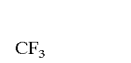 |
| Cl | (2-) Cl | N(CH₃)₂ |  |
| Cl | (2-) Cl | 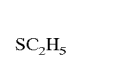 | 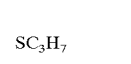 |
| Cl | (2-) Cl | Cl | 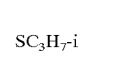 |
| Cl | (2-) Cl | Br | 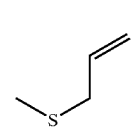 |
| SO₂CH₃ | (2-) Cl | CF₃ | |
| SO₂CH₃ | (2-) Cl | SCH₃ | |
| SO₂CH₃ | (2-) Cl | SC₂H₅ | |
| SO₂CH₃ | (2-) Cl | SC₃H₇ | |
| SO₂CH₃ | (2-) Cl | SC₃H₇-i | |
| SO₂CH₃ | (2-) Cl | | |
| SO₂CH₃ | (2-) Cl | | |
| SO₂CH₃ | (2-) Cl | | |

-continued

| $R^3$ | (position-) $(R^4)_n$ | $R^5$ | $R^6$ |
|---|---|---|---|
| $SO_2CH_3$ | (2-) Cl | -C≡C-S-CH₃ | cyclopropyl |
| $SO_2CH_3$ | (2-) Cl | -CH₂-S-cyclopropyl | cyclopropyl |
| $SO_2CH_3$ | (2-) Cl | SCH=C=CH₂ | cyclopropyl |
| $SO_2CH_3$ | (2-) Cl | $SCH_2CN$ | cyclopropyl |
| $SO_2CH_3$ | (2-) Cl | $SCH_2CH_2CN$ | cyclopropyl |
| $SO_2CH_3$ | (2-) Cl | $OCH_3$ | cyclopropyl |
| $SO_2CH_3$ | (2-) Cl | $OC_2H_5$ | cyclopropyl |
| $SO_2CH_3$ | (2-) Cl | $OC_3H_7$ | cyclopropyl |
| $SO_2CH_3$ | (2-) Cl | $OC_3H_7$-i | cyclopropyl |
| $SO_2CH_3$ | (2-) Cl | $OC_4H_9$ | cyclopropyl |
| $SO_2CH_3$ | (2-) Cl | $OCH_2CF_3$ | cyclopropyl |
| $SO_2CH_3$ | (2-) Cl | -O-CH₂-cyclopropyl | cyclopropyl |
| $SO_2CH_3$ | (2-) Cl | $OC_6H_5$ | cyclopropyl |
| $SO_2CH_3$ | (2-) Cl | H | cyclopropyl |
| $SO_2CH_3$ | (2-) Cl | $CH_3$ | cyclopropyl |
| $SO_2CH_3$ | (2-) Cl | $C_2H_5$ | cyclopropyl |
| $SO_2CH_3$ | (2-) Cl | $C_3H_7$ | cyclopropyl |
| $SO_2CH_3$ | (2-) Cl | $C_3H_7$-i | cyclopropyl |
| $SO_2CH_3$ | (2-) Cl | $C_4H_9$ | cyclopropyl |
| $SO_2CH_3$ | (2-) Cl | $C_4H_9$-i | cyclopropyl |
| $SO_2CH_3$ | (2-) Cl | $C_4H_9$-s | cyclopropyl |
| $SO_2CH_3$ | (2-) Cl | $C_4H_9$-t | cyclopropyl |
| $SO_2CH_3$ | (2-) Cl | cyclopropyl | cyclopropyl |
| $SO_2CH_3$ | (2-) Cl | -CH₂-cyclopropyl | cyclopropyl |
| $SO_2CH_3$ | (2-) Cl | CH=CHCH₃ | cyclopropyl |
| $SO_2CH_3$ | (2-) Cl | phenyl | cyclopropyl |
| $SO_2CH_3$ | (2-) Cl | 4-chlorophenyl | cyclopropyl |
| $SO_2CH_3$ | (2-) Cl | benzyl | cyclopropyl |
| $SO_2CH_3$ | (2-) Cl | $N(CH_3)_2$ | cyclopropyl |
| $SO_2CH_3$ | (2-) Cl | morpholinyl | cyclopropyl |
| $SO_2CH_3$ | (2-) Cl | Cl | cyclopropyl |
| $SO_2CH_3$ | (2-) Cl | Br | cyclopropyl |
| Cl | (2-) $SO_2CH_3$ | $CF_3$ | cyclopropyl |

-continued

| R³ | (position-) (R⁴)ₙ | R⁵ | R⁶ |
|---|---|---|---|
| Cl | (2-) SO₂CH₃ | SCH₃ | cyclopropyl |
| Cl | (2-) SO₂CH₃ | SC₂H₅ | cyclopropyl |
| Cl | (2-) SO₂CH₃ | SC₃H₇ | cyclopropyl |
| Cl | (2-) SO₂CH₃ | SC₃H₇-i | cyclopropyl |
| Cl | (2-) SO₂CH₃ | SCH₂CH=CH₂ | cyclopropyl |
| Cl | (2-) SO₂CH₃ | SCH₂C≡CH | cyclopropyl |
| Cl | (2-) SO₂CH₃ | SCH=CHCH₃ | cyclopropyl |
| Cl | (2-) SO₂CH₃ | SC≡CCH₃ | cyclopropyl |
| Cl | (2-) SO₂CH₃ | SCH₂-cyclopropyl | cyclopropyl |
| Cl | (2-) SO₂CH₃ | SCH=C=CH₂ | cyclopropyl |
| Cl | (2-) SO₂CH₃ | SCH₂CN | cyclopropyl |
| Cl | (2-) SO₂CH₃ | SCH₂CH₂CN | cyclopropyl |
| Cl | (2-) SO₂CH₃ | OCH₃ | cyclopropyl |
| Cl | (2-) SO₂CH₃ | OC₂H₅ | cyclopropyl |
| Cl | (2-) SO₂CH₃ | OC₃H₇ | cyclopropyl |
| Cl | (2-) SO₂CH₃ | OC₃H₇-i | cyclopropyl |
| Cl | (2-) SO₂CH₃ | OC₄H₉ | cyclopropyl |
| Cl | (2-) SO₂CH₃ | OCH₂CF₃ | cyclopropyl |
| Cl | (2-) SO₂CH₃ | OCH₂-cyclopropyl | cyclopropyl |
| Cl | (2-) SO₂CH₃ | OC₆H₅ | cyclopropyl |
| Cl | (2-) SO₂CH₃ | H | cyclopropyl |
| Cl | (2-) SO₂CH₃ | CH₃ | cyclopropyl |
| Cl | (2-) SO₂CH₃ | C₂H₅ | cyclopropyl |
| Cl | (2-) SO₂CH₃ | C₃H₇ | cyclopropyl |
| Cl | (2-) SO₂CH₃ | C₃H₇-i | cyclopropyl |
| Cl | (2-) SO₂CH₃ | C₄H₉ | cyclopropyl |
| Cl | (2-) SO₂CH₃ | C₄H₉-i | cyclopropyl |
| Cl | (2-) SO₂CH₃ | C₄H₉-s | cyclopropyl |
| Cl | (2-) SO₂CH₃ | C₄H₉-t | cyclopropyl |
| Cl | (2-) SO₂CH₃ | cyclopropyl | cyclopropyl |
| Cl | (2-) SO₂CH₃ | CH₂-cyclopropyl | cyclopropyl |
| Cl | (2-) SO₂CH₃ | CH=CHCH₃ | cyclopropyl |

-continued

| R³ | (position-) (R⁴)ₙ | R⁵ | R⁶ |
|---|---|---|---|
| Cl | (2-) SO₂CH₃ |  |  |
| Cl | (2-) SO₂CH₃ | 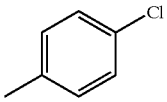 |  |
| Cl | (2-) SO₂CH₃ | 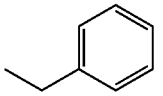 |  |
| Cl | (2-) SO₂CH₃ | N(CH₃)₂ |  |
| Cl | (2-) SO₂CH₃ | 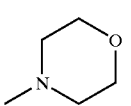 |  |
| Cl | (2-) SO₂CH₃ | Cl |  |
| Cl | (2-) SO₂CH₃ | Br |  |
| Cl | (2-) Cl | CF₃ | N(CH₃)₂ |
| Cl | (2-) Cl | SCH₃ | N(CH₃)₂ |
| Cl | (2-) Cl | SC₂H₅ | N(CH₃)₂ |
| Cl | (2-) Cl | SC₃H₇ | N(CH₃)₂ |
| Cl | (2-) Cl | SC₃H₇-i | N(CH₃)₂ |
| Cl | (2-) Cl | 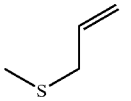 | N(CH₃)₂ |
| Cl | (2-) Cl |  | N(CH₃)₂ |
| Cl | (2-) Cl | 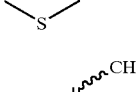 | N(CH₃)₂ |
| Cl | (2-) Cl | 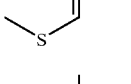 | N(CH₃)₂ |
| Cl | (2-) Cl | 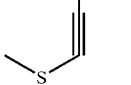 | N(CH₃)₂ |
| Cl | (2-) Cl | SCH=C=CH₂ | N(CH₃)₂ |
| Cl | (2-) Cl | SCH₂CN | N(CH₃)₂ |
| Cl | (2-) Cl | SCH₂CH₂CN | N(CH₃)₂ |
| Cl | (2-) Cl | OCH₃ | N(CH₃)₂ |

-continued

| R³ | (position-) (R⁴)ₙ | R⁵ | R⁶ |
|---|---|---|---|
| Cl | (2-) Cl | OC₂H₅ | N(CH₃)₂ |
| Cl | (2-) Cl | OC₃H₇ | N(CH₃)₂ |
| Cl | (2-) Cl | OC₃H₇-i | N(CH₃)₂ |
| Cl | (2-) Cl | OC₄H₉ | N(CH₃)₂ |
| Cl | (2-) Cl | OCH₂CF₃ | N(CH₃)₂ |
| Cl | (2-) Cl | 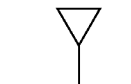 | N(CH₃)₂ |
| Cl | (2-) Cl | OC₆H₅ | N(CH₃)₂ |
| Cl | (2-) Cl | H | N(CH₃)₂ |
| Cl | (2-) Cl | CH₃ | N(CH₃)₂ |
| Cl | (2-) Cl | C₂H₅ | N(CH₃)₂ |
| Cl | (2-) Cl | C₃H₇ | N(CH₃)₂ |
| Cl | (2-) Cl | C₃H₇-i | N(CH₃)₂ |
| Cl | (2-) Cl | C₄H₉ | N(CH₃)₂ |
| Cl | (2-) Cl | C₄H₉-i | N(CH₃)₂ |
| Cl | (2-) Cl | C₄H₉-s | N(CH₃)₂ |
| Cl | (2-) Cl | C₄H₉-t | N(CH₃)₂ |
| Cl | (2-) Cl |  | N(CH₃)₂ |
| Cl | (2-) Cl |  | N(CH₃)₂ |
| Cl | (2-) Cl | CH=CHCH₃ | N(CH₃)₂ |
| Cl | (2-) Cl | 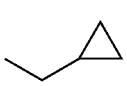 | N(CH₃)₂ |
| Cl | (2-) Cl | 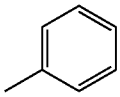 | N(CH₃)₂ |
| Cl | (2-) Cl | 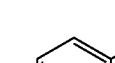 | N(CH₃)₂ |
| Cl | (2-) Cl | N(CH₃)₂ | N(CH₃)₂ |
| Cl | (2-) Cl | 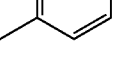 | N(CH₃)₂ |
| Cl | (2-) Cl | Cl | N(CH₃)₂ |
| Cl | (2-) Cl | Br | N(CH₃)₂ |
| SO₂CH₃ | (2-) Cl | CF₃ | N(CH₃)₂ |
| SO₂CH₃ | (2-) Cl | SCH₃ | N(CH₃)₂ |
| SO₂CH₃ | (2-) Cl | SC₂H₅ | N(CH₃)₂ |
| SO₂CH₃ | (2-) Cl | SC₃H₇ | N(CH₃)₂ |
| SO₂CH₃ | (2-) Cl | SC₃H₇-i | N(CH₃)₂ |
| SO₂CH₃ | (2-) Cl | 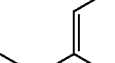 | N(CH₃)₂ |

-continued

| R³ | (position-) (R⁴)ₙ | R⁵ | R⁶ |
|---|---|---|---|
| SO₂CH₃ | (2-) Cl | 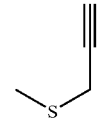 | N(CH₃)₂ |
| SO₂CH₃ | (2-) Cl | 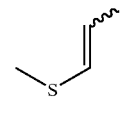 | N(CH₃)₂ |
| SO₂CH₃ | (2-) Cl | 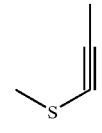 | N(CH₃)₂ |
| SO₂CH₃ | (2-) Cl | 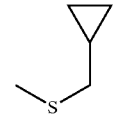 | N(CH₃)₂ |
| SO₂CH₃ | (2-) Cl | SCH=C=CH₂ | N(CH₃)₂ |
| SO₂CH₃ | (2-) Cl | SCH₂CN | N(CH₃)₂ |
| SO₂CH₃ | (2-) Cl | SCH₂CH₂CN | N(CH₃)₂ |
| SO₂CH₃ | (2-) Cl | OCH₃ | N(CH₃)₂ |
| SO₂CH₃ | (2-) Cl | OC₂H₅ | N(CH₃)₂ |
| SO₂CH₃ | (2-) Cl | OC₃H₇ | N(CH₃)₂ |
| SO₂CH₃ | (2-) Cl | OC₃H₇-i | N(CH₃)₂ |
| SO₂CH₃ | (2-) Cl | OC₄H₉ | N(CH₃)₂ |
| SO₂CH₃ | (2-) Cl | OCH₂CF₃ | N(CH₃)₂ |
| SO₂CH₃ | (2-) Cl | 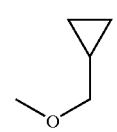 | N(CH₃)₂ |
| SO₂CH₃ | (2-) Cl | OC₆H₅ | N(CH₃)₂ |
| SO₂CH₃ | (2-) Cl | H | N(CH₃)₂ |
| SO₂CH₃ | (2-) Cl | CH₃ | N(CH₃)₂ |
| SO₂CH₃ | (2-) Cl | C₂H₅ | N(CH₃)₂ |
| SO₂CH₃ | (2-) Cl | C₃H₇ | N(CH₃)₂ |
| SO₂CH₃ | (2-) Cl | C₃H₇-i | N(CH₃)₂ |
| SO₂CH₃ | (2-) Cl | C₄H₉ | N(CH₃)₂ |
| SO₂CH₃ | (2-) Cl | C₄H₉-i | N(CH₃)₂ |
| SO₂CH₃ | (2-) Cl | C₄H₉-s | N(CH₃)₂ |
| SO₂CH₃ | (2-) Cl | C₄H₉-t | N(CH₃)₂ |
| SO₂CH₃ | (2-) Cl | 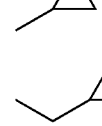 | N(CH₃)₂ |
| SO₂CH₃ | (2-) Cl | 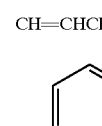 | N(CH₃)₂ |
| SO₂CH₃ | (2-) Cl | CH=CHCH₃ | N(CH₃)₂ |
| SO₂CH₃ | (2-) Cl | 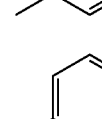 | N(CH₃)₂ |
| SO₂CH₃ | (2-) Cl |  | N(CH₃)₂ |
| SO₂CH₃ | (2-) Cl | 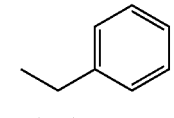 | N(CH₃)₂ |
| SO₂CH₃ | (2-) Cl | N(CH₃)₂ | N(CH₃)₂ |
| SO₂CH₃ | (2-) Cl | 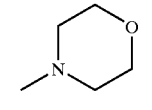 | N(CH₃)₂ |
| SO₂CH₃ | (2-) Cl | Cl | N(CH₃)₂ |
| SO₂CH₃ | (2-) Cl | Br | N(CH₃)₂ |
| Cl | (2-) SO₂CH₃ | CF₃ | N(CH₃)₂ |
| Cl | (2-) SO₂CH₃ | SCH₃ | N(CH₃)₂ |
| Cl | (2-) SO₂CH₃ | SC₂H₅ | N(CH₃)₂ |
| Cl | (2-) SO₂CH₃ | SC₃H₇ | N(CH₃)₂ |
| Cl | (2-) SO₂CH₃ | SC₃H₇-i | N(CH₃)₂ |
| Cl | (2-) SO₂CH₃ | 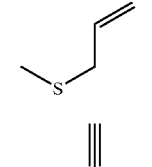 | N(CH₃)₂ |
| Cl | (2-) SO₂CH₃ | 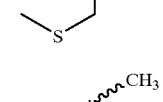 | N(CH₃)₂ |
| Cl | (2-) SO₂CH₃ | 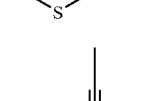 | N(CH₃)₂ |
| Cl | (2-) SO₂CH₃ | 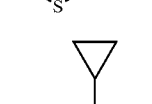 | N(CH₃)₂ |
| Cl | (2-) SO₂CH₃ | 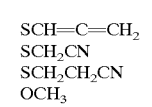 | N(CH₃)₂ |
| Cl | (2-) SO₂CH₃ | SCH=C=CH₂ | N(CH₃)₂ |
| Cl | (2-) SO₂CH₃ | SCH₂CN | N(CH₃)₂ |
| Cl | (2-) SO₂CH₃ | SCH₂CH₂CN | N(CH₃)₂ |
| Cl | (2-) SO₂CH₃ | OCH₃ | N(CH₃)₂ |
| Cl | (2-) SO₂CH₃ | OC₂H₅ | N(CH₃)₂ |
| Cl | (2-) SO₂CH₃ | OC₃H₇ | N(CH₃)₂ |
| Cl | (2-) SO₂CH₃ | OC₃H₇-i | N(CH₃)₂ |
| Cl | (2-) SO₂CH₃ | OCH₄H₉ | N(CH₃)₂ |
| Cl | (2-) SO₂CH₃ | OCH₂CF₃ | N(CH₃)₂ |
| Cl | (2-) SO₂CH₃ | 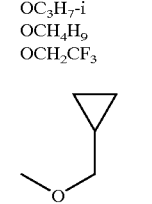 | N(CH₃)₂ |
| Cl | (2-) SO₂CH₃ | OC₆H₅ | N(CH₃)₂ |
| Cl | (2-) SO₂CH₃ | H | N(CH₃)₂ |
| Cl | (2-) SO₂CH₃ | CH₃ | N(CH₃)₂ |
| Cl | (2-) SO₂CH₃ | C₂H₅ | N(CH₃)₂ |
| Cl | (2-) SO₂CH₃ | C₃H₇ | N(CH₃)₂ |
| Cl | (2-) SO₂CH₃ | C₃H₇-i | N(CH₃)₂ |
| Cl | (2-) SO₂CH₃ | C₄H₉ | N(CH₃)₂ |

-continued

| R³ | (position-) (R⁴)ₙ | R⁵ | R⁶ |
|---|---|---|---|
| Cl | (2-) SO₂CH₃ | C₄H₉-i | N(CH₃)₂ |
| Cl | (2-) SO₂CH₃ | C₄H₉-s | N(CH₃)₂ |
| Cl | (2-) SO₂CH₃ | C₄H₉-t | N(CH₃)₂ |
| Cl | (2-) SO₂CH₃ | cyclopropyl | N(CH₃)₂ |
| Cl | (2-) SO₂CH₃ | cyclopropylmethyl | N(CH₃)₂ |
| Cl | (2-) SO₂CH₃ | CH=CHCH₃ | N(CH₃)₂ |
| Cl | (2-) SO₂CH₃ | 4-methylphenyl | N(CH₃)₂ |
| Cl | (2-) SO₂CH₃ | 4-chloro-3-methylphenyl | N(CH₃)₂ |
| Cl | (2-) SO₂CH₃ | benzyl | N(CH₃)₂ |
| Cl | (2-) SO₂CH₃ | N(CH₃)₂ | N(CH₃)₂ |
| Cl | (2-) SO₂CH₃ | 4-methylmorpholinyl | N(CH₃)₂ |
| Cl | (2-) SO₂CH₃ | Cl | N(CH₃)₂ |
| Cl | (2-) SO₂CH₃ | Br | N(CH₃)₂ |
| Cl | (2-) Cl | CH₃ | OCH₃ |
| Cl | (2-) Cl | C₂H₅ | OCH₃ |
| Cl | (2-) Cl | C₃H₇ | OCH₃ |
| Cl | (2-) Cl | SCH₃ | OCH₃ |
| Cl | (2-) Cl | SC₂H₅ | OCH₃ |
| Cl | (2-) Cl | OCH₃ | OCH₃ |
| Cl | (2-) Cl | OC₂H₅ | OCH₃ |
| Cl | (2-) Cl | CH₃ | OC₂H₅ |
| Cl | (2-) Cl | C₂H₅ | OC₂H₅ |
| Cl | (2-) Cl | C₃H₇ | OC₂H₅ |
| Cl | (2-) Cl | SCH₃ | OC₂H₅ |
| Cl | (2-) Cl | SC₂H₅ | OC₂H₅ |
| Cl | (2-) Cl | OCH₃ | OC₂H₅ |
| Cl | (2-) Cl | OC₂H₅ | OC₂H₅ |
| Cl | (2-) SO₂CH₃ | CH₃ | OCH₃ |
| Cl | (2-) SO₂CH₃ | C₂H₅ | OCH₃ |
| Cl | (2-) SO₂CH₃ | C₃H₇ | OCH₃ |
| Cl | (2-) SO₂CH₃ | SCH₃ | OCH₃ |
| Cl | (2-) SO₂CH₃ | SC₂H₅ | OCH₃ |
| Cl | (2-) SO₂CH₃ | OCH₃ | OCH₃ |
| Cl | (2-) SO₂CH₃ | OC₂H₅ | OCH₃ |
| Cl | (2-) SO₂CH₃ | CH₃ | OC₂H₅ |
| Cl | (2-) SO₂CH₃ | C₂H₅ | OC₂H₅ |
| Cl | (2-) SO₂CH₃ | C₃H₇ | OC₂H₅ |
| Cl | (2-) SO₂CH₃ | SCH₃ | OC₂H₅ |
| Cl | (2-) SO₂CH₃ | SC₂H₅ | OC₂H₅ |
| Cl | (2-) SO₂CH₃ | OCH₃ | OC₂H₅ |
| Cl | (2-) SO₂CH₃ | OC₂H₅ | OC₂H₅ |
| SO₂CH₃ | (2-) Cl | Cl | OCH₃ |
| SO₂CH₃ | (2-) Cl | Br | OCH₃ |
| SO₂CH₃ | (2-) Cl | CH₃ | OCH₃ |
| SO₂CH₃ | (2-) Cl | C₂H₅ | OCH₃ |
| SO₂CH₃ | (2-) Cl | C₃H₇ | OCH₃ |
| SO₂CH₃ | (2-) Cl | SCH₃ | OCH₃ |
| SO₂CH₃ | (2-) Cl | SC₂H₅ | OCH₃ |
| SO₂CH₃ | (2-) Cl | OCH₃ | OC₂H₅ |

-continued

| R³ | (position-) (R⁴)ₙ | R⁵ | R⁶ |
|---|---|---|---|
| SO₂CH₃ | (2-) Cl | OC₂H₅ | OC₂H₅ |
| SO₂CH₃ | (2-) Cl | CH₃ | OC₂H₅ |
| SO₂CH₃ | (2-) Cl | C₂H₅ | OC₂H₅ |
| SO₂CH₃ | (2-) Cl | C₃H₇ | OC₂H₅ |
| SO₂CH₃ | (2-) Cl | SCH₃ | OC₂H₅ |
| SO₂CH₃ | (2-) Cl | SC₂H₅ | OC₂H₅ |
| SO₂CH₃ | (2-) Cl | OCH₃ | OC₂H₅ |
| CF₃ | (2-) Cl | Br | CH₃ |
| CF₃ | (2-) Cl | SCH₃ | CH₃ |
| CF₃ | (2-) Cl | OCH₃ | CH₃ |
| CF₃ | (2-) Cl | N(CH₃)₂ | CH₃ |
| CF₃ | (2-) Cl | CF₃ | CH₃ |
| CF₃ | (2-) NO₂ | Br | CH₃ |
| CF₃ | (2-) NO₂ | SCH₃ | CH₃ |
| CF₃ | (2-) NO₂ | OCH₃ | CH₃ |
| CF₃ | (2-) NO₂ | N(CH₃)₂ | CH₃ |
| CF₃ | (2-) NO₂ | CF₃ | CH₃ |
| CF₃ | (2-) CH₃ | Br | CH₃ |
| CF₃ | (2-) CH₃ | SCH₃ | CH₃ |
| CF₃ | (2-) CH₃ | OCH₃ | CH₃ |
| CF₃ | (2-) CH₃ | N(CH₃)₂ | CH₃ |
| CF₃ | (2-) CH₃ | CF₃ | CH₃ |
| CF₃ | (2-) OCH₃ | Br | CH₃ |
| CF₃ | (2-) OCH₃ | SCH₃ | CH₃ |
| CF₃ | (2-) OCH₃ | OCH₃ | CH₃ |
| CF₃ | (2-) OCH₃ | N(CH₃)₂ | CH₃ |
| CF₃ | (2-) OCH₃ | CF₃ | CH₃ |
| SO₂CH₃ | (2-) NO₂ | Br | CH₃ |
| SO₂CH₃ | (2-) NO₂ | SCH₃ | CH₃ |
| SO₂CH₃ | (2-) NO₂ | OCH₃ | CH₃ |
| SO₂CH₃ | (2-) NO₂ | N(CH₃)₂ | CH₃ |
| SO₂CH₃ | (2-) NO₂ | CF₃ | CH₃ |
| SO₂CH₃ | (2-) CF₃ | Br | CH₃ |
| SO₂CH₃ | (2-) CF₃ | SCH₃ | CH₃ |
| SO₂CH₃ | (2-) CF₃ | OCH₃ | CH₃ |
| SO₂CH₃ | (2-) CF₃ | N(CH₃)₂ | CH₃ |
| SO₂CH₃ | (2-) CF₃ | CF₃ | CH₃ |
| SO₂CH₃ | (2-) SO₂CH₃ | Br | CH₃ |
| SO₂CH₃ | (2-) SO₂CH₃ | SCH₃ | CH₃ |
| SO₂CH₃ | (2-) SO₂CH₃ | OCH₃ | CH₃ |
| SO₂CH₃ | (2-) SO₂CH₃ | N(CH₃)₂ | CH₃ |
| SO₂CH₃ | (2-) SO₂CH₃ | CF₃ | CH₃ |
| CN | (2-) Cl | Br | CH₃ |
| CN | (2-) Cl | SCH₃ | CH₃ |
| CN | (2-) Cl | OCH₃ | CH₃ |
| CN | (2-) Cl | N(CH₃)₂ | CH₃ |
| CN | (2-) Cl | CF₃ | CH₃ |
| CN | (2-) NO₂ | Br | CH₃ |
| CN | (2-) NO₂ | SCH₃ | CH₃ |
| CN | (2-) NO₂ | OCH₃ | CH₃ |
| CN | (2-) NO₂ | N(CH₃)₂ | CH₃ |
| CN | (2-) NO₂ | CF₃ | CH₃ |
| CN | (2-) CF₃ | Br | CH₃ |
| CN | (2-) CF₃ | SCH₃ | CH₃ |
| CN | (2-) CF₃ | OCH₃ | CH₃ |
| CN | (2-) CF₃ | N(CH₃)₂ | CH₃ |
| CN | (2-) CF₃ | CF₃ | CH₃ |
| CN | (2-) SO₂CH₃ | Br | CH₃ |
| CN | (2-) SO₂CH₃ | SCH₃ | CH₃ |
| CN | (2-) SO₂CH₃ | OCH₃ | CH₃ |
| CN | (2-) SO₂CH₃ | N(CH₃)₂ | CH₃ |
| CN | (2-) SO₂CH₃ | CF₃ | CH₃ |
| Br | (2-) NO₂ | Br | CH₃ |
| Br | (2-) NO₂ | SCH₃ | CH₃ |
| Br | (2-) NO₂ | OCH₃ | CH₃ |
| Br | (2-) NO₂ | N(CH₃)₂ | CH₃ |
| Br | (2-) NO₂ | CF₃ | CH₃ |
| Br | (2-) CF₃ | Br | CH₃ |
| Br | (2-) CF₃ | SCH₃ | CH₃ |
| Br | (2-) CF₃ | OCH₃ | CH₃ |
| Br | (2-) CF₃ | N(CH₃)₂ | CH₃ |
| Br | (2-) CF₃ | CF₃ | CH₃ |
| Br | (2-) SO₂CH₃ | Br | CH₃ |
| Br | (2-) SO₂CH₃ | SCH₃ | CH₃ |
| Br | (2-) SO₂CH₃ | OCH₃ | CH₃ |
| Br | (2-) SO₂CH₃ | N(CH₃)₂ | CH₃ |
| Br | (2-) SO₂CH₃ | CF₃ | CH₃ |

-continued

| $R^3$ | (position-) $(R^4)_n$ | $R^5$ | $R^6$ |
|---|---|---|---|
| Br | (2-) $CH_3$ | Br | $CH_3$ |
| Br | (2-) $CH_3$ | $SCH_3$ | $CH_3$ |
| Br | (2-) $CH_3$ | $OCH_3$ | $CH_3$ |
| Br | (2-) $CH_3$ | $N(CH_3)_2$ | $CH_3$ |
| Br | (2-) $CH_3$ | $CF_3$ | $CH_3$ |

Group 3

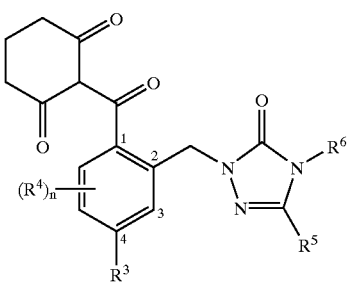
(IA-2)

Here, $R^3$, $(R^4)_n$, $R^5$ and $R^6$ each have, for example, the meanings given above in Group 1.

Group 4

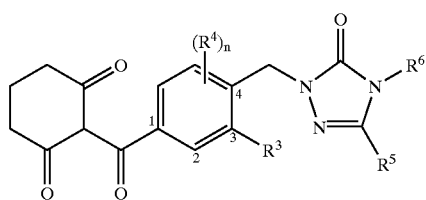
(IC-1)

Here, $R^3$, $(R^4)_n$, $R^5$ and $R^6$ each have, for example, the meanings given above in Group 2.

The novel substituted benzoylcyclohexanediones of the general formula (I) have strong and selective herbicidal activity.

The novel substituted benzoylcyclohexanediones of the general formula (I) are obtained when 1,3-cyclohexanedione or its derivatives of the general formula (II),

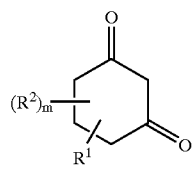
(II)

in which m $R^1$ and $R^2$ are each as defined above.

are reacted with substituted benzoic acids of the general formula (III).

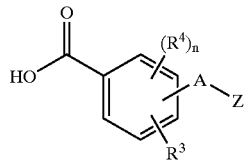
(III)

in which n, A, $R^3$, $R^4$ and Z are each as defined above, in the presence of a dehydrating agent, if appropriate in the presence of one or more reaction auxiliaries and if appropriate in the presence of a diluent, and, if appropriate, the compounds of the formula (I) obtained in this manner are subsequently subjected in a customary manner, within the scope of the definition of the substituents, to electrophilic or nucleophilic or oxidation or reduction reactions, or the compounds of the formula (I) are converted in a customary manner into salts.

The compounds of the formula (I) can be converted into other compounds of the formula (I) in accordance with the definition above using customary methods, for example by nucleophilic substitution (for example $R^5$: $Cl \rightarrow OC_2H_5$, $SCH_3$) or by oxidation (for example $R^5$: $CH_2SCH_3 \rightarrow CH_2S(O)CH_3$).

In principle, the compounds of the general formula (I) can also be synthesized as shown schematically below:

Reaction of 1,3-cyclohexanedione or its derivatives of the general formula (II)—above—with reactive derivatives of the substituted benzoic acids of the general formula (III)—above—in particular with the corresponding carbonyl chlorides, carboxylic anhydrides, carboxylic acid cyanides, methyl carboxylates or ethyl carboxylates—if appropriate in the presence of reaction auxiliaries, such as, for example, triethylamine (and, if appropriate, additionally zinc chloride), and, if appropriate, in the presence of a diluent, such as, for example, methylene chloride:

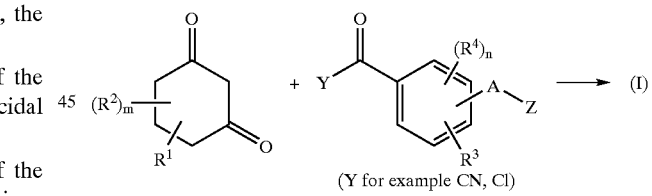

(Y for example CN, Cl)

In the reactions outlined above for preparing the compounds of the general formula (I), there is, in addition to the desired C-benzoylation at the cyclohexanedione, also an O-benzoylation—cf. equation below (cf. Synthesis 1978, 925–927; Tetrahedron Lett. 37 (1996), 1007–1009, WO-A-91/05469). However, the O-benzoyl compounds formed in this process are, under the reaction conditions of the process according to the invention, isomerized to the corresponding C-benzoyl compounds of the formula (I).

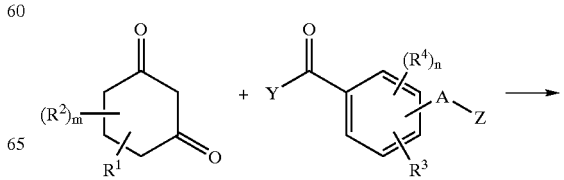

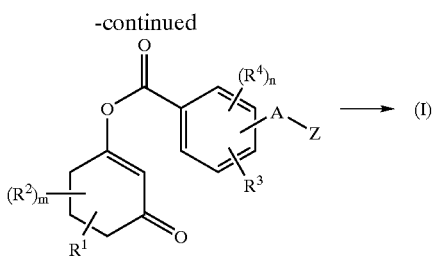 (I)

Using, for example, 1,3-cyclohexanedione and 2-(3-carboxy-5-fluorobenzyl)-5-ethyl-4-methoxy-2,4-dihydro-3H-1,2,4-triazol-3-one as starting materials, the course of the reaction in the process according to the invention can be outlined by the following equation:

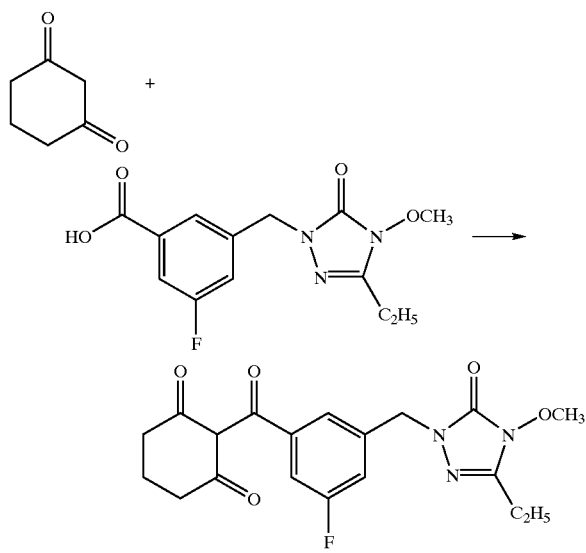

The formula (II) provides a general definition of the cyclohexanediones to be used as starting materials in the process according to the invention for preparing compounds of the formula (I). In the formula (II), m, $R^1$ and $R^2$ each preferably have those meanings which have already been given above, in connection with the description of the compounds of the formula (I) according to the invention, as being preferred, as being particularly preferred, or as being very particularly preferred for m, $R^1$ and $R^2$.

The starting materials of the general formula (II) are known and/or can be prepared by processes known per se.

The formula (III) provides a general definition of the substituted benzoic acids further to be used as starting materials in the process according to the invention for preparing compounds of the formula (I). In the formula (III), n, A, $R^3$, $R^4$ and Z each preferably have those meanings which have already been given above, in connection with the description of the compounds of the formula (I) according to the invention, as being preferred, as being particularly preferred, as being very particularly preferred or as being most preferred for n, A, $R^3$, $R^4$ and Z.

Except for 2-(5-carboxy-2,4-dichloro-phenyl)-4-difluoromethyl-5-methyl-2,4-dihydro-3H-1,2,4-triazol-3-one-alias 2,4-dichloro-5-(4-difluoromethyl-4,5-dihydro-3-methyl-5-oxo-1H-1,2,4-triazol-1-yl)-benzoic acid (CAS-Reg.-No. 90208-77-8) and 2-(5-carboxy-2,4-dichloro-phenyl)-4,5-dimethyl-2,4-dihydro-3H-1,2,4-triazol-3-one-alias 2,4-dichloro-5-(4,5-dihydro-3,4-dimethyl-5-oxo-1H-1,2,4-triazol-1-yl)-benzoic acid (CAS-Reg.-No. 90208-76-7)—the starting materials of the general formula (III) have hitherto not been disclosed in the literature. Except for 2-(5-carboxy-2,4-dichloro-phenyl)-4-difluoromethyl-5-methyl-2,4-dihydro-3H-1,2,4-triazol-3-one and 2-(5-carboxy-2,4-dichloro-phenyl)-4,5-dimethyl-2,4-dihydro-3H-1,2,4-triazol-3-one (cf. JP-A-58225070—quoted in Chem. Abstracts 100:209881, JP-A-02015069—quoted in Chem. Abstracts 113:23929), they also form, as novel compounds, part of the subject matter of the present application.

The novel substituted benzoic acids of the general formula (III), are obtained when benzoic acid derivatives of the general formula (IV),

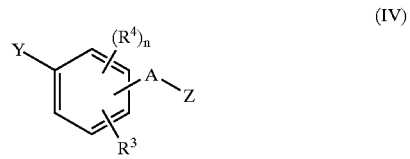 (IV)

in which
n, A, $R^3$ and $R^4$ and Z are each as defined above, and
Y represents cyano, carbamoyl, halogenocarbamoyl or alkoxycarbonyl,
are reacted with water, if appropriate in the presence of a hydrolysis auxiliary, such as, for example, sulphuric acid, at temperatures between 50° C. and 120° C. (cf. the Preparation Examples).

The benzoic acid derivatives of the general formula (IV) required as precursors are known and/or can be prepared by processes known per se (cf. DE-A-3839480 DE-A-4239296. EP-A-597360, EP-A-609734, DE-A4303676. EP-A-617026, DE-A-4405614. U.S. Pat. No. 5,378,681).

The novel substituted benzoic acids of the general formula (III) are also obtained when halogeno(alkyl)benzoic acids of the general formula (V),

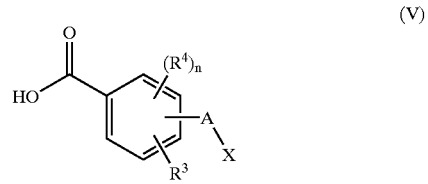 (V)

in which
n, A, $R^3$ and $R^4$ are each as defined above and
X represents halogen (in particular fluorine, chlorine or bromine)
are reacted with compounds of the general formula (VI)

 (VI)

in which
Z is as defined above,
if appropriate in the presence of a reaction auxiliary, such as, for example, triethylamine or potassium carbonate, and if appropriate in the presence of a diluent, such as, for example, acetone, acetonitrile, N,N-dimethyl-formamide or N,N-dimethyl-acetamide, at temperatures between 50° C. and 200° C. (cf. the Preparation Examples).

Instead of the halogeno(alkyl)benzoic acids of the general formula (V), it is also possible, similarly to the methods described above, to react appropriate nitrites, amides and esters—in particular the methyl esters or the ethyl esters—with compounds of the general formula (VI). By subsequent hydrolysis according to customary methods, for example by reaction with aqueous-ethanolic potassium hydroxide solution, it is then possible to obtain the corresponding substituted benzoic acids.

The halogeno(alkyl)benzoic acids of the formula (V)—or corresponding nitriles or esters—required as precursors are known and/or can be prepared by processes known per se (cf. EP-A-90369, EP-A-93488, EP-A-399732, EP-A-480641. EP-A-609798. EP-A-763524, DE-A-2126720, WO-A-93103722. WO-A-97/38977. U.S. Pat. No. 3,978, 127, U.S. Pat. No. 4,837,333).

The compounds of the general formula (VI) further required as precursors are known and/or can be prepared by processes known per se.

The process according to the invention for preparing the novel substituted benzoylcyclohexanediones of the general formula (I) is carried out using a dehydrating agent. Here, suitable dehydrating agents are the customary chemicals which are suitable for binding water.

Examples of these are dicyclohexylcarbodiimide and carbonyl-bis-imidazole.

A particularly suitable dehydrating agent is dicyclohexylcarbodiimide.

The process according to the invention for preparing novel substituted benzoylcyclohexanediones of the general formula (I) is, if appropriate, carried out using a reaction auxiliary.

Examples of these are sodium cyanide, potassium cyanide, acetone cyanohydrin, 2-cyano-2-(trimethylsilyloxy)-propane and trimethylsilyl cyanide.

The particularly suitable further reaction auxiliary is trimethylsilyl cyanide.

The process according to the invention for preparing the novel substituted benzoylcyclohexanediones of the general formula (I) is, if appropriate, carried out using a further reaction auxiliary. Suitable further reaction auxiliaries for the process according to the invention are, in general, basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methylpiperidine, 1,4-diazabicyclo[2,2,2]-octane (DABCO), 1,5-diazabicyclo[4,3,0]-non-5-ene (DBN), or 1,8-diazabicyclo[5.4.0]-undec-7-ene (DBU).

Suitable diluents for carrying out the process according to the invention are, in particular, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane or 1,2-dichloroethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethyl-phosphoric triamide; esters such as methyl acetate or ethyl acetate, sulphoxides, such as dimethylsulphoxide.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry, out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a dehydrating agent, and the reaction mixture is generally stirred at the required temperature for several hours. Work-up is carried out by customary methods (cf. the Preparation Examples).

The active compounds according to the invention can be used as defoliants, desiccants, haulm killers and, especially, as weedkillers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.*

Monocotyledonous weeds of the genera: *Echinochloa, Setaria Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Monocotyledonous crops of the genera: *Oryza, Zea, Triticum, Hordeum, Avena, Secale, Sorghum, Panicum, Saccharum, Ananas, Asparagus, Allium.*

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and open spaces with or without tree plantings. Equally, the compounds can be employed for the control of weeds in perennial crops for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture land, and for the selective control of weeds in annual crops.

The compounds of the formula (I) according to the invention are particularly suitable for the selective control of monocotyledonous and dicotyledonous weeds in monocotyledonous crops, both pre-emergence and postemergence.

The active compounds can be converted into the customary formulations such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifying agents and/or dispersing agents and/or foam-forming agents.

If the extender used is water, it is also possible to employ for example organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates: suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For the control of weeds, the active compounds according to the invention, as such or in the form of their formulations, can also be used as mixtures with known herbicides, finished formulations or tank mixes being possible.

Possible components for the mixtures are known herbicides, for example
acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron (-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl). 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop (-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate-(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), procarbazone, prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 and 10 kg of active compound per hectare of soil surface, preferably between 5 g and 5 kg per ha.

The preparation and use of the active compounds according to the invention can be seen from the following examples.

PREPARATION EXAMPLES

Example 1

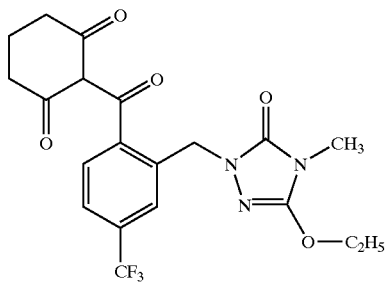

1.2 g (3.48 mmol) of 5-ethoxy-4-methyl-2-(2-carboxy-5-trifluoromethyl-benzyl)-2,4-dihydro-3H-1,2,4-triazol-3-one are suspended in 30 ml of acetonitrile and, at room temperature (approximately 20° C.), admixed with 0.39 g (3.48 mmol) of 1,3-cyclohexanedione and 0.76 g (3.7 mmol) of dicyclohexylcarbodiimide (DCC). The reaction mixture is stirred at room temperature overnight (approximately 15 hours) and then admixed with 1.0 ml (7.0 mmol) of triethylamine and 0.10 ml (1.39 mmol) of trimethylsilyl cyanide. After 3 hours at room temperature, the mixture is stirred with 100 ml of 5% strength aqueous sodium carbonate solution, the dicyclohexylurea that separates out is filtered off with suction and the alkaline aqueous phase is repeatedly extracted with ethyl acetate. The aqueous phase is then adjusted to pH 2 using 35% strength hydrochloric acid and extracted repeatedly with methylene chloride. The methylene chloride phases are dried over sodium sulphate and concentrated.

This gives 0.8 g (52% of theory) of 5-ethoxy-4-methyl-2-[2-(2,6-dioxo-cyclohexyl-carbonyl)-5-trifluoromethyl-benzyl]-2,4-dihydro-3H-1,2,4-triazol-3-one as an amorphous residue.

logP (determined at pH=2): 2.70.

Example 2

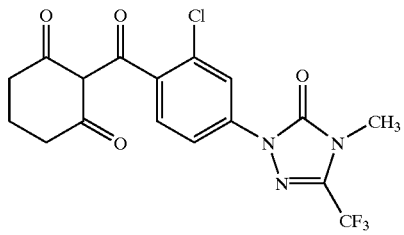

A solution of 1.5 g (7.2 mmol) of dicyclohexylcarbodiimide in 40 ml of acetonitrile is added to a suspension of 2.15 g (6.5 mmol) of 2-(4-carboxy-3-chloro-phenyl)-4-methyl-5-trifluoromethyl-2,4-dihydro-3H-1,2,4-triazol-3-one, 0.83 g (7.2 mmol) of 1,3-cyclohexanedione and 40 ml of acetonitrile, and the reaction mixture is stirred at 20° C. for 16 hours. 1.3 g (13 mmol) of triethylamine and 0.26 g (2.6 mmol) of trimethylsilyl cyanide are then added, and the reaction mixture is stirred at 20° C. for a further 4 hours. The mixture is then stirred with 180 ml of 2% strength aqueous sodium carbonate solution and filtered off with suction. The mother liquor is extracted with ethyl acetate. The aqueous phase is then acidified using 2N hydrochloric acid and extracted with methylene chloride. The organic phase is dried, concentrated under water pump vacuum and digested with diethyl ether/petroleum ether. The resulting crystalline product is isolated by filtration with suction.

This gives 1.6 g (59% of theory) of 2-[4-(2,6-dioxocyclohexylcarbonyl)-3-chloro-phenyl]4-methyl-5-trifluoromethyl-2,4-dihydro-3H-1,2,4-triazol-3'-one of melting point 182° C.

logP (determined at pH=2): 3.13.

By the methods of Preparation Examples 1 and 2, and in accordance with the general description of the preparation processes according to the invention, it is also possible to prepare, for example, the compounds of the formula (I)— or of the formulae (IA-3), (IB-2), (IC-2) or (ID)—listed in Tables 1 and 2 below.

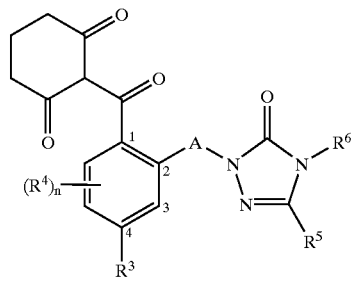

(IA-3)

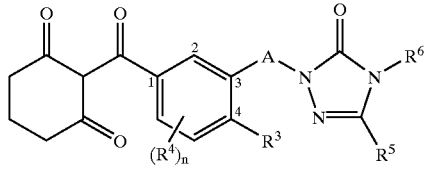

(IB-2)

-continued

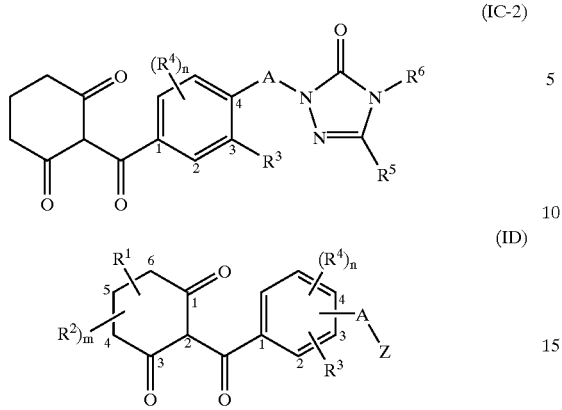

TABLE 1

Examples of compounds of the formulae (IA-3), (IB-2), (IC-2)

| Ex. No. | A | $R^3$ | (position) $(R^4)_n$ | $R^5$ | $R^6$ | (formula) physical data |
|---|---|---|---|---|---|---|
| 3 | — | H | H | $CF_3$ | $CH_3$ | (IC-2) logP = 2.41[a] |
| 4 | $CH_2$ | $CF_3$ | H | △ | △ | (IA-3) logP = 2.41[a] |
| 5 | $CH_2$ | $SO_2CH_3$ | H | △ | △ | (IB-2) m.p.: 153° C. |
| 6 | $CH_2$ | $SO_2CH_3$ | H | $CH_3$ | $CH_3$ | (IA-3) m.p.: 162° C. |
| 7 | $CH_2$ | Cl | H | $CH_3$ | $CH_3$ | (IB-2) logP = 1.50[a] |
| 8 | $CH_2$ | Cl | H | $CF_3$ | $CH_3$ | (IB-2) logP = 2.44[a] |
| 9 | $CH_2$ | Cl | H | △ | △ | (IB-2) logP = 2.23[b] |
| 10 | $CH_2$ | Br | H | $C_2H_5$ | $OC_2H_5$ | (IA-3) logP = 2.68[a] |
| 11 | $CH_2$ | F | H | $OC_2H_5$ | $CH_3$ | (IA-3) logP = 1.73[a] |
| 12 | $CH_2$ | F | H | $SCH_3$ | $CH_3$ | (IA-3) logP = 1.99[a] |
| 13 | $CH_2$ | F | H | $SO_2CH_3$ | $CH_3$ | (IA-3) logP = 1.83[a] |
| 14 | $CH_2$ | Br | H | $CH_3$ | $CH_3$ | (IB-2) logP = 1.57[a] |
| 15 | $CH_2$ | Br | H | $OC_2H_5$ | $CH_3$ | (IB-2) m.p.: 132° C. |
| 16 | $CH_2$ | Br | H | △ | △ | (IB-2) logP = 2.31[a] |
| 17 | $CH_2$ | Cl | H | $OC_2H_5$ | △ | (IA-3) logP = 3.03[a] |
| 18 | $CH_2$ | Cl | H | $CF_3$ | $CH_3$ | (IA-3) logP = 2.75[a] |
| 19 | $CH_2$ | Cl | H | $C_2H_5$ | $OC_2H_5$ | (IA-3) logP = 2.60[a] |
| 20 | $CH_2$ | $NO_2$ | H | $SCH_3$ | $CH_3$ | (IA-3) |

TABLE 1-continued

Examples of compounds of the formulae (IA-3), (IB-2), (IC-2)

| Ex. No. | A | $R^3$ | (position) $(R^4)_n$ | $R^5$ | $R^6$ | (formula) physical data |
|---|---|---|---|---|---|---|
| | | | | | | logP = 2.04[a] |
| 21 | $CH_2$ | $CF_3$ | H | $OC_2H_5$ |  | (IA-3) logP = 3.02[a] |
| 22 | $CH_2$ | $CF_3$ | H | $C_2H_5$ | $OC_2H_5$ | (IA-3) logP = 2.91[a] |
| 23 | $CH_2$ | $CF_3$ | H | $SCH_3$ | $CH_3$ | (IA-3) logP = 2.59[a] |
| 24 | $CH_2$ | $OCH_3$ | H | $OC_2H_5$ | $CH_3$ | (IA-3) logP = 1.99[a] |
| 25 | $CH_2$ | $OCH_3$ | H | $C_2H_5$ | $OC_2H_5$ | (IA-3) logP = 2.18[a] |
| 26 | $CH_2$ | Br | H | $OC_2H_5$ | $CH_3$ | (IA-3) logP = 2.46[a] |
| 27 | $CH_2$ | Br | H | $CF_3$ | $CH_3$ | (IA-3) logP = 2.85[a] |
| 28 | $CH_2$ | H | H | $CF_3$ | $CH_3$ | (IA-3) logP = 2.33[a] |
| 29 | $CH_2$ | $CF_3$ | H | $OCH_3$ | $CH_3$ | (IA-3) logP = 2.35[a] |
| 30 | $CH_2$ | F | H | $CF_3$ | $CH_3$ | (IA-3) logP = 2.47[a] |
| 31 | $CH_2$ | F | H | $C_2H_5$ | $OC_2H_5$ | (IA-3) logP = 2.28[a] |
| 32 | $CH_2$ | F | H | $OCH_3$ | $CH_3$ | (IA-3) logP = 1.76[a] |
| 33 | $CH_2$ | H | H | $OC_2H_5$ | $CH_3$ | (IA-3) logP = 1.93[a] |
| 34 | $CH_2$ | H | H | $OCH_3$ | $CH_3$ | (IA-3) logP = 1.61[a] |
| 35 | — | H | (2) $CF_3$ | $CF_3$ | $CH_3$ | (IC-2) m.p.: 190° C. |
| 36 | — | H | H | $CF_3$ | $CH_3$ | (IA-3) logP = 2.48[a] |
| 37 | — | Cl | H | $CF_3$ | $CH_3$ | (IA-3) logP = 2.83[a] |
| 38 | — | H | (2) Cl | $CH_3$ | $CH_3$ | (IC-2) m.p.: 196° C. |
| 39 | $CH_2$ | Cl | (2) Cl | $CF_3$ | $CH_3$ | (IB-2) logP = 2.79[a] |
| 40 | — | Br | H | $CF_3$ | $CH_3$ | (IA-3) logP = 2.90[a] |
| 41 | $CH_2$ | Cl | (2) Cl | $SCH_3$ | $CH_3$ | (IB-2) logP = 2.38[a] |
| 42 | $CH_2$ | Cl | (2) Cl | $OC_2H_5$ | $CH_3$ | (IB-2) logP = 2.48[a] |
| 43 | $CH_2$ | Cl | (2) Cl |  |  | (IB-2) logP = 2.62[a] |
| 44 | $CH_2$ | Cl | (2) Cl | $OCH_3$ | $CH_3$ | (IB-2) logP = 2.14[a] |
| 45 | $CH_2$ | Cl | (2) Cl | $OC_3H_7$-i | $CH_3$ | (IB-2) logP = 2.79[a] |
| 46 | $CH_2$ | Cl | (2) Cl | $OCH_2CF_3$ | $CH_3$ | (IB-2) logP = 2.84[a] |
| 47 | $CH_2$ | Cl | (2) Cl | Br | $CH_3$ | (IB-2) logP = 2.26[a] |
| 48 | $CH_2$ | Cl | (2) Cl | H | $CH_3$ | (IB-2) logP = 1.69[a] |
| 49 | $CH_2$ | Cl | (2) Cl |  | $CH_3$ | (IB-2) logP = 2.25[a] |
| 50 | $CH_2$ | Cl | (2) Cl | $N(CH_3)_2$ | $CH_3$ | (IB-2) logP = 2.18[a] |
| 51 | $CH_2$ | Cl | (2) Cl | $CH_3$ | $CH_3$ | (IB-2) logP = 1.79[a] |
| 52 | $CH_2$ | Cl | (2) Cl | $R^5 + R^6$: | $(CH_2)_4$ | (IB-2) |

TABLE 1-continued

Examples of compounds of the formulae (IA-3), (IB-2), (IC-2)

| Ex. No. | A | R³ | (position) (R⁴)ₙ | R⁵ | R⁶ | (formula) physical data |
|---|---|---|---|---|---|---|
| | | | | | | logP = 1.98[a)] |
| 53 | $CH_2$ | Cl | (2) Cl | $OCH_3$ |  | (IB-2) logP = 2.45[a)] |
| 54 | $CH_2$ | Cl | (2) Cl | $OC_2H_5$ |  | (IB-2) logP = 2.79[a)] |
| 55 | $CH_2$ | Cl | (2) Cl | $OC_3H_7$-i |  | (IB-2) logP = 3.14[a)] |
| 56 | $CH_2$ | Cl | (2) Cl | $OCH_2CF_3$ |  | (IB-2) logP = 3.18[a)] |
| 57 | $CH_2$ | Cl | (2) Cl | $SCH_3$ |  | (IB-2) logP = 2.77[a)] |
| 58 | $CH_2$ | Cl | (2) Cl | $N(CH_3)_2$ |  | (IB-2) logP = 2.49[a)] |
| 59 | $CH_2$ | Cl | (2) Cl | $CH_3$ |  | (IB-2) logP = 2.09[a)] |
| 60 | $CH_2$ | Cl | (2) Cl | $C_2H_5$ | $OC_2H_5$ | (IB-2) logP = 2.65[a)] |
| 61 | $CH_2$ | $CF_3$ | H | $CF_3$ | $CH_3$ | (IA-3) logP = 3.06[a)] |
| 62 | $CH_2$ | H | H | $C_2H_5$ | $OC_2H_5$ | (IA-3) logP = 2.10[a)] |
| 63 | $CH_2$ | H | H | $SCH_3$ | $CH_3$ | (IA-3) logP = 1.85[a)] |
| 64 | $CH_2$ | H | H |  |  | (IA-3) logP = 2.09[a)] |
| 65 | $CH_2$ | Cl | (5) Cl | $CF_3$ | $CH_3$ | (IA-3) logP = 3.24[a)] |
| 66 | $CH_2$ | H | H | $SO_2CH_3$ | $CH_3$ | (IA-3) logP = 1.71[a)] |
| 67 | $CH_2$ | $SO_2CH_3$ | H | $OC_2H_5$ | $CH_3$ | (IA-3) logP = 1.64[a)] |
| 68 | $CH_2$ | Br | H | R⁷ + R⁶: | $(CH_2)_4$ | (IA-3) logP = 1.64[a)] |
| 69 | $CH_2$ | Br | H | $OC_3H_7$-n | $CH_3$ | (IA-3) logP = 2.82[a)] |
| 70 | $CH_2$ | Br | H | $OC_3H_7$-i | $CH_3$ | (IA-3) logP = 2.84[a)] |
| 71 | $CH_2$ | $CF_3$ | H | $OC_3H_7$-i | $CH_3$ | (IA-3) logP = 3.05[a)] |
| 72 | $CH_2$ | $CF_3$ | H | $OC_3H_7$-n | $CH_3$ | (IA-3) logP = 3.06[a)] |
| 73 | $CH_2$ | Br | H | Br | $CH_3$ | (IA-3) logP = 2.33[a)] |
| 74 | $CH_2$ | $CF_3$ | H | $OC_3H_7$-i |  | (IA-3) logP = 3.38[a)] |
| 75 | $CH_2$ | $CF_3$ | H | $CH_2OCH_3$ |  | (IA-3) logP = 2.53[a)] |
| 76 | $CH_2$ | $CF_3$ | H | $CH_2OCH_3$ | $CH_3$ | (IA-3) |

TABLE 1-continued

Examples of compounds of the formulae (IA-3), (IB-2), (IC-2)

| Ex. No. | A | R³ | (position) (R⁴)ₙ | R⁵ | R⁶ | (formula) physical data |
|---|---|---|---|---|---|---|
| 77 | CH₂ | I | H | CF₃ | CH₃ | (IA-3) logP = 2.26[a] |
| 78 | CH₂ | Br | H | SCH₃ | CH₃ | (IA-3) logP = 2.98[a] |
| 79 | CH₂ | Cl | H | SCH₃ | CH₃ | (IA-3) logP = 2.36[a] |
| 80 | CH₂ | CF₃ | H | CH₃ | CH₃ | (IA-3) logP = 2.30[a] |
| 81 | CH₂ | CF₃ | H | OC₂H₅ | C₂H₅ | (IA-3) logP = 2.06[a] |
| 82 | CH₂ | CF₃ | H | N(CH₃)₂ | CH₃ | (IA-3) logP = 3.01[a] |
| 83 | CH₂ | CF₃ | H | Br | CH₃ | (IA-3) logP = 2.40[a] |
| 84 | CH₂ | H | (3) CH₃ | OC₂H₅ | CH₃ | (IA-3) logP = 2.54[a] |
| 85 | CH₂ | Br | H |  | 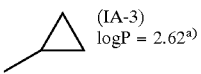 | (IA-3) logP = 2.21[a] |
| 86 | CH₂ | Br | H | 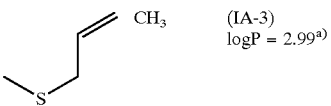 | | (IA-3) logP = 2.62[a] |
| 87 | CH₂ | CF₃ | H | SC₂H₅ | CH₃ | (IA-3) logP = 2.99[a] |
| 88 | CH₂ | CF₃ | H | SC₃H₇-i | CH₃ | (IA-3) logP = 2.94[a] |
| 89 | CH₂ | CF₃ | H | R⁵ + R⁶: | (CH₂)₄ | (IA-3) logP = 2.63[a] |
| 90 | CH₂ | CF₃ | H | OCH₃ | 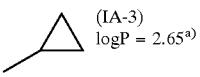 | (IA-3) logP = 2.25[a] |
| 91 | CH₂ | CF₃ | H | OCH₂CF₃ | CH₃ | (IA-3) logP = 2.65[a] |
| 92 | CH₂ | CN | H | CF₃ | CH₃ | (IA-3) logP = 3.06[a] |
| 93 | CH₂ | F | H | N(CH₃)₂ | CH₃ | (IA-3) logP = 2.29[a] |
| 94 | CH₂ | F | H | OC₃H₇-n | CH₃ | (IA-3) logP = 1.81[a] |
| 95 | CH₂ | F | H | CH₂OCH₃ | CH₃ | (IA-3) logP = 2.44[a] |
| 96 | CH₂ | F | H | OCH₃ | 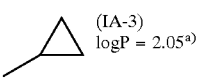 | (IA-3) logP = 1.69[a] |
| 97 | CH₂ | F | H | OC₂H₅ | 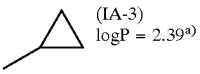 | (IA-3) logP = 2.05[a] |
| 98 | CH₂ | I | H | OC₂H₅ | CH₃ | (IA-3) logP = 2.39[a] |
| 99 | CH₂ | OCH₃ | (2) NO₂ | OC₂H₅ | CH₃ | (IC-2) logP = 2.59[a] |
| 100 | CH₂ | OCH₃ | (2) NO₂ | SCH₃ | CH₃ | (IC-2) logP = 2.24[a] |
| | | | | | | logP = 2.18[a] |

TABLE 2

Examples of compounds of the formula (ID)

| Ex. No. | A | (position) R¹ | (position) (R²)ₘ | (position) R³ | (position) (R⁴)ₙ | (position) Z | physical data |
|---|---|---|---|---|---|---|---|
| ID-1 | $CH_2$ | H | H | (2) Cl | (4) Cl | 1,3-dimethyl-tetrahydro-1,3-diazin-2-one (3) | logP = 4.26[a] |
| ID-2 | $CH_2$ | (5) $CH_3$ | (5) $CH_3$ | (4) $CF_3$ | H | 2,4,5-trimethyl-2,4-dihydro-3H-1,2,4-triazol-3-one (2) | logP = 2.61[a] |
| ID-3 | $CH_2$ | H | H | (4) $CF_3$ | H | 1,2,4-trimethyl-1,2,4-triazolidine-3,5-dione (2) | logP = 2.24[a] |
| ID-4 | $CH_2$ | H | H | (4) $CF_3$ | H | 2,4,4,5-tetramethyl-2,4-dihydro-3H-pyrazol-3-one (2) | logP = 2.63[a] |
| ID-5 | $CH_2$ | H | H | H | H | 3-methyl-benzo[d][1,2,3]triazin-4(3H)-one (2) | logP = 2.35[a] |
| ID-6 | $CH_2$ | H | H | (4) $CF_3$ | H | 3-methyl-5-(trifluoromethyl)-1,3,4-thiadiazol-2(3H)-one (2) | logP = 3.77[a] |
| ID-7 | $CH_2$ | (5) $CH_3$ | (5) $CH_3$ | (4) $CF_3$ | H | 5-ethoxy-2,4-dimethyl-2,4-dihydro-3H-1,2,4-triazol-3-one (2) | logP = 3.27[a] |

TABLE 2-continued
Examples of compounds of the formula (ID)
| Ex. No. | A | (position) R¹ | (position) (R²)ₘ | (position) R³ | (position) (R⁴)ₙ | (position) Z | physical data |
|---|---|---|---|---|---|---|---|
| ID-8 | $CH_2$ | (5) $CH_3$ | (5) $CH_3$ | (4) $CF_3$ | H | 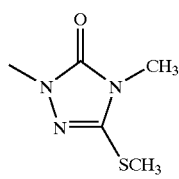 (2) | logP = 3.18[a)] |
| ID-9 | $CH_2$ | H | H | (4) Br | H | 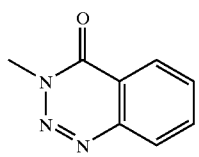 (2) | logP = 2.92[a)] |
| ID-10 | $CH_2$ | H | H | (4) Br | H | 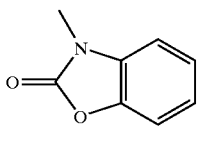 (2) | logP = 3.04[a)] |
| ID-11 | $CH_2$ | (5) $CH_3$ | (5) $CH_3$ | (2) Cl | (4) Cl | 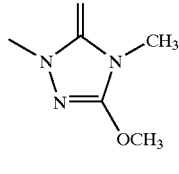 (3) | m.p.: 140° C. logP = 2.72[a)] |
| ID-12 | $CH_2$ | (5) $CH_3$ | (5) $CH_3$ | (2) Cl | (4) Cl | 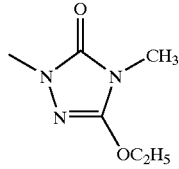 (3) | m.p.: 103° C. logP = 3.08[a)] |
| ID-13 | $CH_2$ | (5) $CH_3$ | (5) $CH_3$ | (2) Cl | (4) Cl | 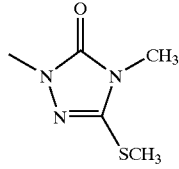 (3) | m.p.: 118° C. logP = 2.98[a)] |
| ID-14 | $CH_2$ | (5) $CH_3$ | (5) $CH_3$ | (2) Cl | (4) Cl | 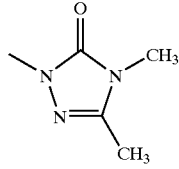 (3) | m.p.: 132° C. logP = 2.32[a)] |

TABLE 2-continued

Examples of compounds of the formula (ID)

| Ex. No. | A | (position) R$^1$ | (position) (R$^2$)$_m$ | (position) R$^3$ | (position) (R$^4$)$_n$ | (position) Z | physical data |
|---|---|---|---|---|---|---|---|
| ID-15 | CH$_2$ | (5) CH$_3$ | (5) CH$_3$ | (2) Cl | (4) Cl | (3) 1-methyl-4-methyl-5-bromo-1,2,4-triazol-3(4H)-one | m.p.: 170° C. logP = 2.86[a)] |
| ID-16 | CH$_2$ | (4) CH$_3$ | (4) CH$_3$ | (2) Cl | (4) Cl | (3) 1-methyl-4-methyl-5-methoxy-1,2,4-triazol-3(4H)-one | logP = 2.78[a)] |
| ID-17 | CH$_2$ | (4) CH$_3$ | (4) CH$_3$ | (2) Cl | (4) Cl | (3) 1-methyl-4-methyl-5-ethoxy-1,2,4-triazol-3(4H)-one | logP = 3.15[a)] |
| ID-18 | CH$_2$ | (4) CH$_3$ | (4) CH$_3$ | (2) Cl | (4) Cl | (3) 1-methyl-4-methyl-5-methylthio-1,2,4-triazol-3(4H)-one | logP = 3.06[a)] |
| ID-19 | CH$_2$ | (4) CH$_3$ | (4) CH$_3$ | (2) Cl | (4) Cl | (3) 1-methyl-4-methyl-5-methyl-1,2,4-triazol-3(4H)-one | logP = 2.38[a)] |
| ID-20 | CH$_2$ | (4) CH$_3$ | (4) CH$_3$ | (2) Cl | (4) Cl | (3) 1-methyl-4-methyl-5-bromo-1,2,4-triazol-3(4H)-one | logP = 2.94[a)] |
| ID-21 | CH$_2$ | (5) C$_3$H$_7$-i | H | (2) Cl | (4) Cl | (3) 1-methyl-4-methyl-5-methoxy-1,2,4-triazol-3(4H)-one | logP = 3.12[a)] |

TABLE 2-continued

Examples of compounds of the formula (ID)

| Ex. No. | A | (position) R$^1$ | (position) (R$^2$)$_m$ | (position) R$^3$ | (position) (R$^4$)$_n$ | (position) Z | physical data |
|---|---|---|---|---|---|---|---|
| ID-22 | CH$_2$ | (5) C$_3$H$_7$-i | H | (2) Cl | (4) Cl | (3) 2-methyl-4-methyl-5-ethoxy-2,4-dihydro-3H-1,2,4-triazol-3-one | logP = 3.49$^{a)}$ |
| ID-23 | CH$_2$ | (5) C$_3$H$_7$-i | H | (2) Cl | (4) Cl | (3) 2-methyl-4-methyl-5-methylthio-2,4-dihydro-3H-1,2,4-triazol-3-one | logP = 3.39$^{a)}$ |
| ID-24 | CH$_2$ | (5) C$_3$H$_7$-i | H | (2) Cl | (4) Cl | (3) 2,4,5-trimethyl-2,4-dihydro-3H-1,2,4-triazol-3-one | logP = 2.70$^{a)}$ |
| ID-25 | CH$_2$ | (5) C$_3$H$_7$-i | H | (2) Cl | (4) Cl | (3) 2-methyl-4-methyl-5-bromo-2,4-dihydro-3H-1,2,4-triazol-3-one | logP = 3.28$^{a)}$ |
| ID-26 | CH$_2$ | (5) CH$_3$ | H | (2) Cl | (4) Cl | (3) 2-methyl-4-methyl-5-methoxy-2,4-dihydro-3H-1,2,4-triazol-3-one | |
| ID-27 | CH$_2$ | (5) CH$_3$ | H | (2) Cl | (4) Cl | (3) 2-methyl-4-methyl-5-ethoxy-2,4-dihydro-3H-1,2,4-triazol-3-one | |
| ID-28 | CH$_2$ | (5) CH$_3$ | H | (2) Cl | (4) Cl | (3) 2-methyl-4-methyl-5-methylthio-2,4-dihydro-3H-1,2,4-triazol-3-one | |

TABLE 2-continued

Examples of compounds of the formula (ID)

| Ex. No. | A | (position) R¹ | (position) (R²)ₘ | (position) R³ | (position) (R⁴)ₙ | (position) Z | physical data |
|---|---|---|---|---|---|---|---|
| ID-29 | $CH_2$ | (5) $CH_3$ | H | (2) Cl | (4) Cl | 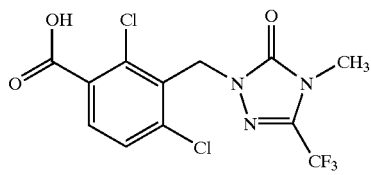 (3) | |
| ID-30 | $CH_2$ | (5) $CH_3$ | H | (2) Cl | (4) Cl | 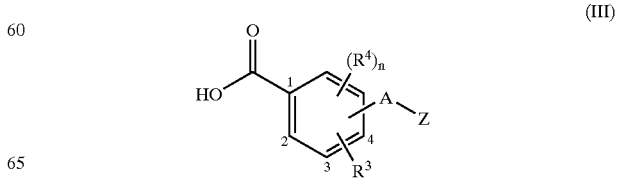 (3) | |

Starting Materials of Formula (III):

Example (III-1)

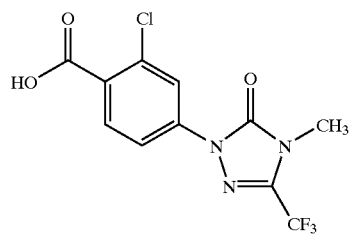

4.5 g (15 mmol) of 2-(3-chloro-4-cyano-phenyl)-4-methyl-5-trifluoromethyl-2.4-dihydro-3H-1,2,4-triazol-3-one are taken up in 80 ml of 60% strength sulphuric acid, and the mixture is heated under reflux for 6 hours. After cooling to room temperature, the resulting crystalline produce is isolated by filtration with suction.

This gives 4.5 g (91% of theory) of 2-(3-carboxy-4-chloro-phenyl)₄-methyl-5-trifluoromethyl-2,4-dihydro-3H-1,2,4-triazol-3-one of melting point 223° C.

Example (III-2)

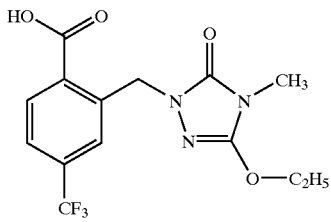

2 g (4.9 mmol) of 5-bromo-4-methyl-2-(2-ethoxycarbonyl-5-trifluoromethyl-benzyl)-2,4-dihydro-3H-1,2,4-triazol-3-one (compare Example IV-1) are dissolved in 30 ml of 10% strength ethanolic potassium hydroxide solution and heated under reflux for 2 hours. The reaction mixture is concentrated under water pump vacuum, taken up in 20 ml of water and acidified with dilute hydrochloric acid. The solid that precipitates out is filtered and dried.

This gives 1.2 g (71% of theory) of 5-ethoxy-4-methyl-2-(2-carboxy-5-trifluoro-methyl-benzyl)-2,4-dihydro-3H-1,2,4-triazol-3-one as a solid product.

logP: 2.18ᵃ)

Example (III-3)

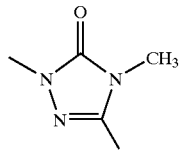

13.4 g (35 mmol) 4-methyl-5-trifluoromethyl-2-(2,6-dichloro-3-methoxycarbonyl-benzyl)-2,4-dihydro-3H-1,2,4-triazol-3-one are initially charged in 60 ml of 1,4-dioxane, and a solution of 1.54 g (38,5 mmol) of sodium hydroxide in 20 ml of water is slowly metered in at room temperature. The reaction mixture is stirred at 60° C. for 150 minutes and subsequently concentrated under water pump vacuum. The residue is dissolved in 100 ml of water, and the pH of the solution is adjusted to 1 by addition of conc. hydrochloric acid. The resulting crystalline product is isolated by filtration with suction.

This gives 11.7 g (90% of theory) of 4-methyl-5-trifluoromethyl-2-(2,6-dichloro-3-carboxy-benzyl)-2,4-dihydro-3H-1,2,4-triazol-3-one of melting point 207° C.

By the methods of Examples (III-1) and (III-3), it is also possible to prepare, for example, the compounds of the general formula (III) listed in Table 2 below.

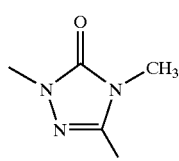
(III)

TABLE 2

Examples of compounds of the formula (III)

| Ex. No. | (position-) R³ | (position-) (R⁴)ₙ | (position-) -A–Z | physical data |
|---|---|---|---|---|
| III-4 | (4-) Cl | H | (2-) triazolinone with N-ethyl, N-CH₃, 5-CH₃ | logP = 1.39[a] |
| III-5 | (4-) SO₂CH₃ | H | (3-) triazolinone with N-ethyl, N-cyclopropyl, 5-cyclopropyl | logP = 1.47[a] |
| III-6 | (4-) F | H | (2-) triazolinone with N-ethyl, N-CH₃, 5-OC₂H₅ | logP = 1.73[a] |
| III-7 | (4-) CF₃ | H | (2-) triazolinone with N-ethyl, N-cyclopropyl, 5-Br | logP = 1.65[a] |
| III-8 | (4-) Br | H | (2-) triazolinone with N-ethyl, N-CH₃, 5-N(CH₃)₂ | logP = 1.74[a] |
| III-9 | (4-) CF₃ | H | (2-) triazolinone with N-ethyl, N-C₂H₅, 5-OC₂H₅ | logP = 2.43[a] |
| III-10 | (4-) CF₃ | H | (2-) triazolinone with N-ethyl, N-C₂H₅, 5-OCH₃ | logP = 2.12[a] |

TABLE 2-continued

Examples of compounds of the formula (III)

| Ex. No. | (position-) R³ | (position-) (R⁴)ₙ | (position-) -A–Z | physical data |
|---|---|---|---|---|
| III-11 | (4-) CF₃ | H | (2-) 1-ethyl-4-methyl-5-methyl-1,2,4-triazol-3(4H)-one | logP = 1.61[a] |
| III-12 | (4-) CF₃ | H | (2-) 1-ethyl-4-methyl-5-(dimethylamino)-1,2,4-triazol-3(4H)-one | logP = 1.93[a] |
| III-13 | (4-) CF₃ | H | (2-) 1-ethyl-4-methyl-5-bromo-1,2,4-triazol-3(4H)-one | logP = 2.01[a] |
| III-14 | (4-) CF₃ | H | (2-) 2-ethylphthalimide | logP = 1.77[a] |
| III-15 | (3-) CH₃ | H | (2-) 1-ethyl-4-methyl-5-ethoxy-1,2,4-triazol-3(4H)-one | logP = 1.70[a] |
| III-16 | (4-) SO₂CH₃ | H | (2-) 1-ethyl-4-methyl-5-methylthio-1,2,4-triazol-3(4H)-one | logP = 1.07[a] |
| III-17 | (4-) CF₃ | H | (2-) 1-ethyl-4-methyl-5-ethylthio-1,2,4-triazol-3(4H)-one | logP = 2.35[a] |

TABLE 2-continued
Examples of compounds of the formula (III)
| Ex. No. | (position-) R³ | (position-) (R⁴)ₙ | (position-) -A–Z | physical data |
|---|---|---|---|---|
| III-18 | (4-) CF₃ | H | (2-) 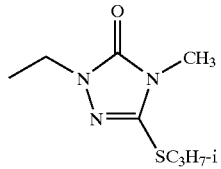 | logP = 2.63[a] |
| III-19 | (4-) CF₃ | H | (2-) 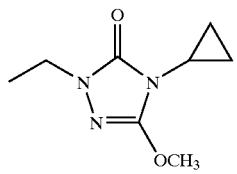 | logP = 2.13[a] |
| III-20 | (4-) CF₃ | H | (2-) 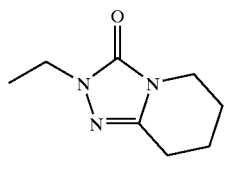 | logP = 1.82[a] |
| III-21 | (4-) CF₃ | H | (2-) 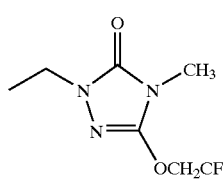 | logP = 2.48[a] |
| III-22 | (4-) CF₃ | H | (2-) 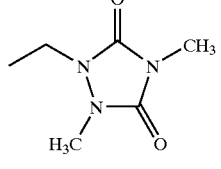 | logP = 1.73[a] |
| III-23 | (4-) CF₃ | H | (2-) 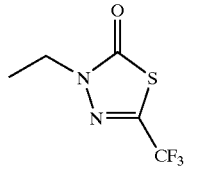 | logP = 3.11[a] |
| III-24 | (4-) F | H | (2-) 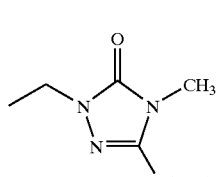 | logP = 1.43[a] |

TABLE 2-continued

Examples of compounds of the formula (III)

| Ex. No. | (position-) R³ | (position-) (R⁴)ₙ | (position-) -A–Z | physical data |
|---|---|---|---|---|
| III-25 | (4-) F | H | (2-) 1-ethyl-4-methyl-5-(n-propoxy)-1,2,4-triazol-3(4H)-one | logP = 1.97[a] |
| III-26 | (4-) F | H | (2-) 1-ethyl-4-methyl-5-(methoxymethyl)-1,2,4-triazol-3(4H)-one | logP = 1.30[a] |
| III-27 | (4-) F | H | (2-) 4-cyclopropyl-1-ethyl-5-methoxy-1,2,4-triazol-3(4H)-one | logP = 1.63[a] |
| III-28 | (4-) F | H | (2-) 4-cyclopropyl-5-ethoxy-1-ethyl-1,2,4-triazol-3(4H)-one | logP = 1.93[a] |
| III-29 | (4-) CF₃ | H | (2-) 2-ethyl-4,4,5-trimethyl-pyrazol-3(4H)-one | logP = 1.78[a] |
| III-30 | (2-) Cl | (4-) Cl | (3-) 1-ethyl-4-methyl-5-(methylthio)-1,2,4-triazol-3(4H)-one | m.p.: 230° C. logP = 1.63[a] |
| III-31 | (2-) Cl | (4-) Cl | (3-) 5-ethoxy-1-ethyl-4-methyl-1,2,4-triazol-3(4H)-one | m.p.: 190° C. logP = 1.73[a] |

TABLE 2-continued

Examples of compounds of the formula (III)

| Ex. No. | (position-) R³ | (position-) (R⁴)ₙ | (position-) -A–Z | physical data |
|---|---|---|---|---|
| III-32 | (2-) Cl | (4-) Cl | (3-) 2-ethyl-4-cyclopropyl-5-cyclopropyl-2,4-dihydro-3H-1,2,4-triazol-3-one | m.p.: 210° C. logP = 1.87[a] |
| III-33 | (2-) Cl | (4-) Cl | (3-) 2-ethyl-4-methyl-5-methoxy-2,4-dihydro-3H-1,2,4-triazol-3-one | m.p.: 210° C. logP = 1.43[a] |
| III-34 | (2-) Cl | (4-) Cl | (3-) 2-ethyl-4-methyl-5-(i-propoxy)-2,4-dihydro-3H-1,2,4-triazol-3-one | m.p.: 164° C. logP = 2.01[a] |
| III-35 | (2-) Cl | (4-) Cl | (3-) 2-ethyl-4-methyl-5-(OCH₂CF₃)-2,4-dihydro-3H-1,2,4-triazol-3-one | m.p.: 168° C. logP = 2.04[a] |
| III-36 | (2-) Cl | (4-) Cl | (3-) 2-ethyl-4-methyl-5-bromo-2,4-dihydro-3H-1,2,4-triazol-3-one | m.p.: 218° C. logP = 1.53[a] |
| III-37 | (2-) Cl | (4-) Cl | (3-) 2-ethyl-4-methyl-2,4-dihydro-3H-1,2,4-triazol-3-one | m.p.: 259° C. logP = 0.98[a] |
| III-38 | (2-) Cl | (4-) Cl | (3-) 2-ethyl-4-methyl-5-cyclopropyl-2,4-dihydro-3H-1,2,4-triazol-3-one | m.p.: 210° C. logP = 1.56[a] |

TABLE 2-continued
Examples of compounds of the formula (III)
| Ex. No. | (position-) R³ | (position-) (R⁴)ₙ | (position-) -A–Z | physical data |
|---|---|---|---|---|
| III-39 | (2-) Cl | (4-) Cl | (3-) 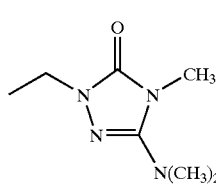 | m.p.: 197° C. logP = 1.51[a)] |
| III-40 | (2-) Cl | (4-) Cl | (3-) 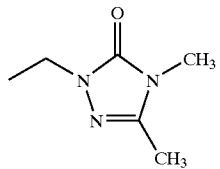 | m.p.: 262° C. logP = 1.11[a)] |
| III-41 | (2-) Cl | (4-) Cl | (3-) 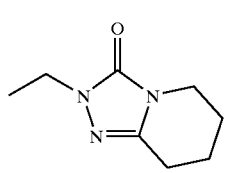 | m.p.: 249° C. logP = 1.30[a)] |
| III-42 | (2-) Cl | (4-) Cl | (3-) 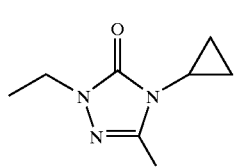 | m.p.: 200° C. logP = 1.71[a)] |
| III-43 | (2-) Cl | (4-) Cl | (3-) 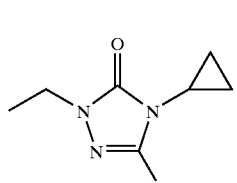 | m.p.: 189° C. logP = 2.01[a)] |
| III-44 | (2-) Cl | (4-) Cl | (3-) 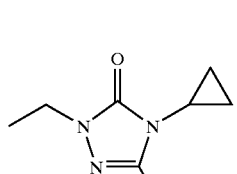 | m.p.: 178° C. logP = 2.28[a)] |
| III-45 | (2-) Cl | (4-) Cl | (3-) 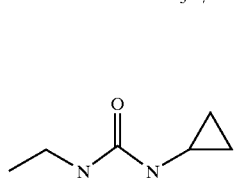 | m.p.: 161° C. logP = 2.31[a)] |

TABLE 2-continued
Examples of compounds of the formula (III)
| Ex. No. | (position-) R³ | (position-) (R⁴)ₙ | (position-) -A–Z | physical data |
|---|---|---|---|---|
| III-46 | (2-) Cl | (4-) Cl | (3-) 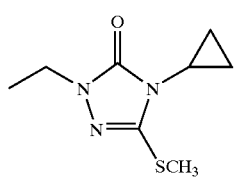 | m.p.: 200° C. logP = 1.98[a)] |
| III-47 | (2-) Cl | (4-) Cl | (3-) 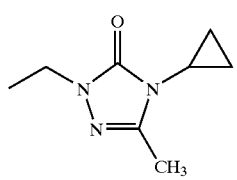 | m.p.: 201° C. logP = 1.39[a)] |
| III-48 | (2-) Cl | (4-) Cl | (3-) 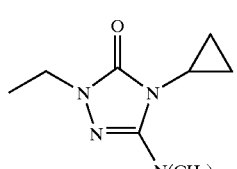 | m.p.: 207° C. logP = 1.77[a)] |
| III-49 | (2-) Cl | (4-) Cl | (3-) 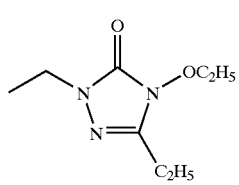 | m.p.: 140° C. logP = 1.88[a)] |
| III-50 | (4-) OCH₂CHF₂ | H | (2-) 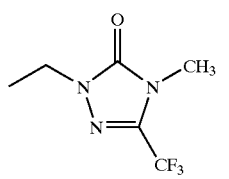 | m.p.: 154° C. logP = 2.14[a)] |
| III-51 | H | H | (2-) 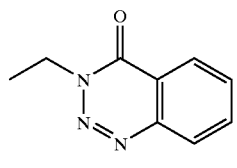 | m.p.: 214° C. logP = 1.87[a)] |
| III-52 | H | H | (2-) 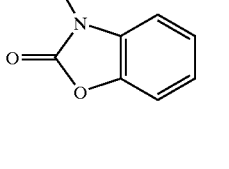 | m.p.: 194° C. logP = 2.07[a)] |

TABLE 2-continued
Examples of compounds of the formula (III)
| Ex. No. | (position-) R³ | (position-) (R⁴)ₙ | (position-) -A–Z | physical data |
|---|---|---|---|---|
| III-53 | H | H | 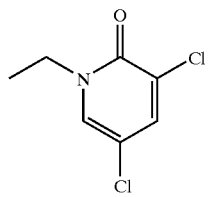 (2-) | m.p.: 181° C. logP = 1.97[a] |
| III-54 | H | H | 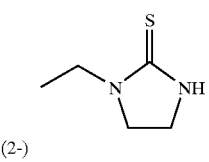 (2-) | m.p.: 251° C. logP = 1.14[a] |
| III-55 | (2-) Cl | (4-) Cl | 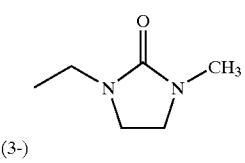 (3-) | logP = 1.38[a] |
| III-56 | (2-) Cl | (4-) Cl | 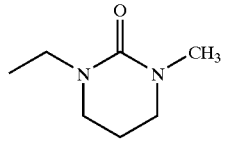 (3-) | logP = 1.48[a] |
| III-57 | (2-) Cl | (4-) Cl | 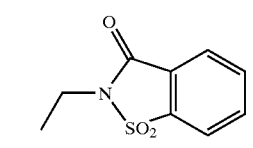 (3-) | |
| III-58 | (4-) Cl | H | 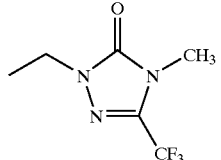 (2-) | ¹H NMR (DMSO-D6, δ): 5.42 ppm. |
| III-59 | (4-) CF₃ | H | 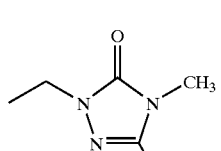 (2-) | ¹H NMR (DMSO-D6, δ): 5.48 ppm. |

TABLE 2-continued

Examples of compounds of the formula (III)

| Ex. No. | (position-) R³ | (position-) (R⁴)ₙ | (position-) -A–Z | physical data |
|---|---|---|---|---|
| III-60 | (4-) CF₃ | H | 1-ethyl-4-methyl-5-(trifluoromethyl)-1,2,4-triazol-3(4H)-one (2-) | $^1$H NMR (DMSO-D6, δ): 5.60 ppm. LogP = 2.47[a] |
| III-61 | (4-) CF₃ | H | 4-cyclopropyl-5-cyclopropyl-1-ethyl-1,2,4-triazol-3(4H)-one (2-) | logP = 2.33[a] |
| III-62 | (4-) SO₂CH₃ | H | 1-ethyl-4-methyl-5-(trifluoromethyl)-1,2,4-triazol-3(4H)-one (3-) | $^1$H NMR (DMSO-D6, δ): 5.14 ppm. |
| III-63 | (4-) SO₂CH₃ | H | 1-ethyl-4,5-dimethyl-1,2,4-triazol-3(4H)-one (2-) | $^1$H NMR (DMSO-D6, δ): 5.27 ppm. |
| III-64 | (4-) Cl | H | 1-ethyl-4,5-dimethyl-1,2,4-triazol-3(4H)-one (3-) | $^1$H NMR (CDCl₃, δ): 5.12 ppm. |
| III-65 | (4-) Cl | H | 1-ethyl-4-methyl-5-(trifluoromethyl)-1,2,4-triazol-3(4H)-one (3-) | $^1$H NMR (DMSO-D6, δ): 5.20 ppm. |

TABLE 2-continued
Examples of compounds of the formula (III)
| Ex. No. | (position-) R³ | (position-) (R⁴)ₙ | (position-) -A–Z | physical data |
|---|---|---|---|---|
| III-66 | (4-) Cl | H | (2-) 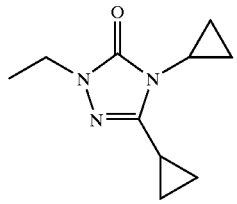 | $^1$H NMR (DMSO-D6, δ): 5.03 ppm. |
| III-67 | (4-) Br | H | (2-) 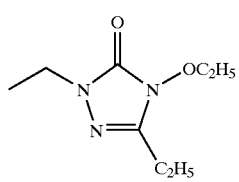 | $^1$H NMR (DMSO-D6, δ): 5.24 ppm. |
| III-68 | (4-) Br | H | (2-) 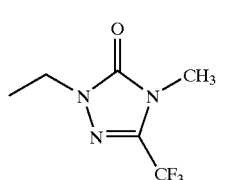 | $^1$H NMR (DMSO-D6, δ): 5.39 ppm. |
| III-69 | (4-) F | H | (2-) 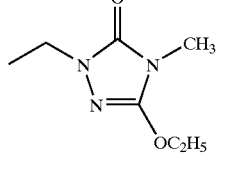 | $^1$H NMR (DMSO-D6, δ): 5.19 ppm. |
| III-70 | (4-) F | H | (2-) 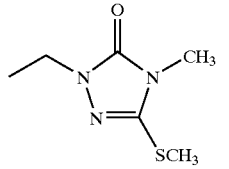 | $^1$H NMR (DMSO-D6, δ): 5.30 ppm. |
| III-71 | (4-) F | H | (2-) 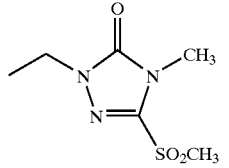 | $^1$H NMR (DMSO-D6, δ): 5.43 ppm. |
| III-72 | (4-) Br | H | (3-) 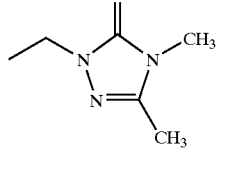 | $^1$H NMR (CDCl₃, δ): 5.10 ppm. |

TABLE 2-continued
Examples of compounds of the formula (III)
| Ex. No. | (position-) R³ | (position-) (R⁴)ₙ | (position-) -A–Z | physical data |
|---|---|---|---|---|
| III-73 | (4-) Br | H | 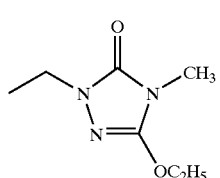 (3-) | ¹H NMR (DMSO-D6, δ): 5.03 ppm. |
| III-74 | (4-) Br | H | 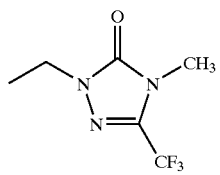 (3-) | ¹H NMR (DMSO-D6, δ): 5.19 ppm. |
| III-75 | (4-) Br | H | 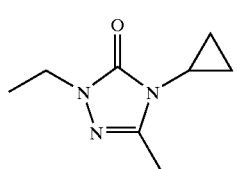 (2-) | ¹H NMR (DMSO-D6, δ): 5.01 ppm. |
| III-76 | (4-) Cl | H | 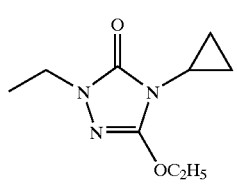 (2-) | ¹H NMR (DMSO-D6, δ): 5.14 ppm. |
| III-77 | (4-) Cl | H | (2-) 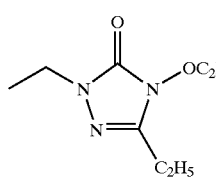 | ¹H NMR (DMSO-D6, δ): 5.25 ppm. |
| III-78 | (4-) NO₂ | H | 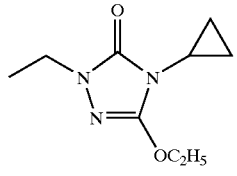 (2-) | ¹H NMR (DMSO-D6, δ): 5.23 ppm. |

TABLE 2-continued
Examples of compounds of the formula (III)
| Ex. No. | (position-) R³ | (position-) (R⁴)ₙ | (position-) -A–Z | physical data |
|---|---|---|---|---|
| III-79 | (4-) NO₂ | H | (2-) 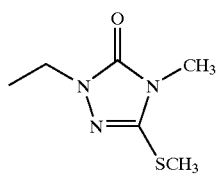 | ¹H NMR (DMSO-D6, δ): 5.37 ppm. |
| III-80 | (4-) CF₃ | H | (2-) 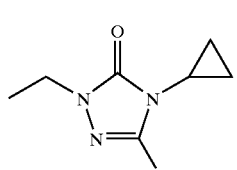 | logP = 2.46[a) |
| III-81 | (4-) CF₃ | H | (2-) 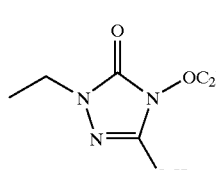 | ¹H NMR (DMSO-D6, δ): 5.31 ppm. |
| III-82 | (4-) CF₃ | H | (2-) 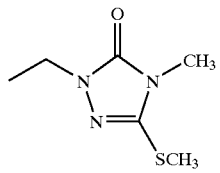 | logP = 2.08[a) |
| III-83 | (4-) OCH₃ | H | (2-) 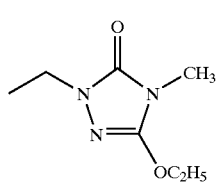 | ¹H NMR (CDCl₃, δ): 5.38 ppm. |
| III-84 | (4-) OCH₃ | H | (2-) 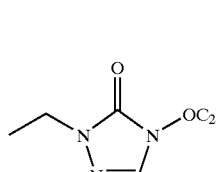 | ¹H NMR (CDCl₃, δ): 5.43 ppm. |
| III-85 | (4-) CF₃ | H | (2-) 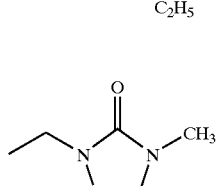 | ¹H NMR (CDCl₃, δ): 5.47 ppm. |

TABLE 2-continued

Examples of compounds of the formula (III)

| Ex. No. | (position-) R³ | (position-) (R⁴)ₙ | (position-) -A–Z | physical data |
|---|---|---|---|---|
| III-86 | (4-) Br | H | (2-) [2-ethyl-6,7-dihydro-5H-pyrrolo[2,1-c][1,2,4]triazol-3(2H)-one] | LogP = 1.44[a] |
| III-87 | (4-) Br | H | (2-) [2-ethyl-5,6,7,8-tetrahydro[1,2,4]triazolo[4,3-a]pyridin-3(2H)-one] | LogP = 1.63[a] |
| III-88 | (4-) Br | H | (2-) [2-ethyl-4-methyl-5-(isopropoxy)-2,4-dihydro-3H-1,2,4-triazol-3-one] | LogP = 2.27[a] |
| III-89 | (4-) Br | H | (2-) [2-ethyl-4-methyl-5-(n-propoxy)-2,4-dihydro-3H-1,2,4-triazol-3-one] | LogP = 2.31[a] |
| III-90 | H | H | (2-) [2-ethyl-4-methyl-5-(trifluoromethyl)-2,4-dihydro-3H-1,2,4-triazol-3-one] | LogP = 1.82[a] |
| III-91 | (4-) Br | H | (2-) [2-ethyl-4-methyl-5-(ethoxy)-2,4-dihydro-3H-1,2,4-triazol-3-one] | ¹H NMR (CDCl₃, δ): 5.32 ppm. |
| III-92 | (4-) Br | H | (2-) [2-ethyl-4-methyl-5-(trifluoromethyl)-2,4-dihydro-3H-1,2,4-triazol-3-one] | ¹H NMR (CDCl₃, δ): 5.53 ppm. |

TABLE 2-continued
Examples of compounds of the formula (III)
| Ex. No. | (position-) $R^3$ | (position-) $(R^4)_n$ | (position-) -A-Z | physical data |
|---|---|---|---|---|
| III-93 | (4-) F | H | 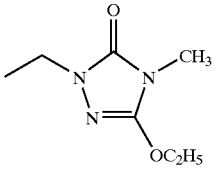 (2-) | $^1$H NMR (CDCl$_3$, δ): 5.39 ppm. |
| III-94 | (4-) F | H | 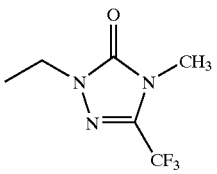 (2-) | $^1$H NMR (CDCl$_3$, δ): 5.57 ppm. |
| III-95 | (4-) F | H | (2-) 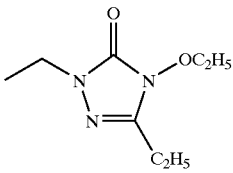 | $^1$H NMR (CDCl$_3$, δ): 5.44 ppm. |
| III-96 | (4-) F | H | 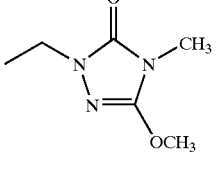 (2-) | $^1$H NMR (CDCl$_3$, δ): 5.41 ppm. |
| III-97 | H | H | 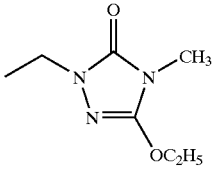 (2-) | $^1$H NMR (CDCl$_3$, δ): 5.34 ppm. |
| III-98 | H | H | 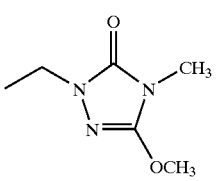 (2-) | $^1$H NMR (CDCl$_3$, δ): 5.38 ppm. |
| III-99 | H | H | 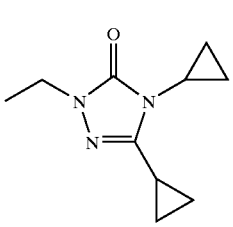 (2-) | $^1$H NMR (CDCl$_3$, δ): 5.26 ppm. |

TABLE 2-continued

Examples of compounds of the formula (III)

| Ex. No. | (position-) R³ | (position-) (R⁴)ₙ | (position-) -A–Z | physical data |
|---|---|---|---|---|
| III-100 | H | H | (2-) 1-ethyl-4-methyl-5-(methylthio)-2,4-dihydro-3H-1,2,4-triazol-3-one | ¹H NMR (CDCl₃, δ): 5.43 ppm. |
| III-101 | H | H | (2-) 1-ethyl-4-methyl-5-(methylsulfonyl)-2,4-dihydro-3H-1,2,4-triazol-3-one | LogP = 1.23[a)] |
| III-102 | (4-) SO₂CH₃ | H | (2-) 5-ethoxy-1-ethyl-4-methyl-2,4-dihydro-3H-1,2,4-triazol-3-one | logP = 1.14[a)] |
| III-103 | (4-) CF₃ | H | (2-) 1-ethyl-5-isopropoxy-4-methyl-2,4-dihydro-3H-1,2,4-triazol-3-one | logP = 2.45[a)] |
| III-104 | (4-) CF₃ | H | (2-) 1-ethyl-4-methyl-5-n-propoxy-2,4-dihydro-3H-1,2,4-triazol-3-one | logP = 2.48[a)] |
| III-105 | (4-) Br | H | (2-) 5-bromo-1-ethyl-4-methyl-2,4-dihydro-3H-1,2,4-triazol-3-one | logP = 1.85[a)] |
| III-106 | (4-) CF₃ | H | (3-) 4-cyclopropyl-1-ethyl-5-isopropoxy-2,4-dihydro-3H-1,2,4-triazol-3-one | logP = 2.74[a)] |

TABLE 2-continued

Examples of compounds of the formula (III)

| Ex. No. | (position-) $R^3$ | (position-) $(R^4)_n$ | (position-) -A–Z | physical data |
|---|---|---|---|---|
| III-107 | (4-) CF$_3$ | H | (2-) [1-ethyl-4-cyclopropyl-5-(methoxymethyl)-1,2,4-triazol-3(4H)-one] | logP = 2.01[a] |
| III-108 | (4-) CF$_3$ | H | (2-) [1-ethyl-4-methyl-5-(methoxymethyl)-1,2,4-triazol-3(4H)-one] | logP = 1.79[a] |
| III-109 | (4-) CF$_3$ | H | (2-) [1-ethyl-4-methyl-5-bromo-1,2,4-triazol-3(4H)-one] | logP = 1.65[a] |
| III-110 | (4-) Br | H | (2-) [1-ethyl-4-methyl-5-(methylthio)-1,2,4-triazol-3(4H)-one] | logP = 1.90[a] |
| III-111 | (4-) Cl | H | (2-) [1-ethyl-4-methyl-5-(methylthio)-1,2,4-triazol-3(4H)-one] | logP = 1.83[a] |
| III-112 | (4-) I | H | (2-) [1-ethyl-4-methyl-5-ethoxy-1,2,4-triazol-3(4H)-one] | logP = 2.06[a] |
| III-113 | (4-) I | H | (2-) [1-ethyl-4-methyl-5-ethyl-1,2,4-triazol-3(4H)-one] | |

TABLE 2-continued

Examples of compounds of the formula (III)

| Ex. No. | (position-) R³ | (position-) (R⁴)ₙ | (position-) -A–Z | physical data |
|---|---|---|---|---|
| III-114 | (4-) Br | H | 2-ethyl-phthalazin-1(2H)-one (2-) | m.p.: 191° C. |
| III-115 | (4-) Br | H | 3-ethyl-benzo[d][1,2,3]triazin-4(3H)-one (2-) | m.p.: 213° C. |
| III-116 | H | H | 2-ethyl-isoindoline-1,3-dione (2-) | |
| III-117 | H | H | 2-ethyl-4-methyl-5-(trifluoromethyl)-2,4-dihydro-3H-1,2,4-triazol-3-one (2-) | m.p.: 112° C. |
| III-118 | (4-) CF₃ | H | 2-ethyl-4-methyl-5-(trifluoromethyl)-2,4-dihydro-3H-1,2,4-triazol-3-one (2-) | m.p.: 158° C. |
| III-119 | (4-) CF₃ | H | 4-cyclopropyl-5-cyclopropyl-2-ethyl-2,4-dihydro-3H-1,2,4-triazol-3-one (2-) | m.p.: 162° C. |
| III-120 | (4-) Cl | (5-) Cl | 2-ethyl-4-methyl-5-(trifluoromethyl)-2,4-dihydro-3H-1,2,4-triazol-3-one (2-) | m.p.: 167° C. |

TABLE 2-continued

Examples of compounds of the formula (III)

| Ex. No. | (position-) R³ | (position-) (R⁴)ₙ | (position-) -A–Z | physical data |
|---|---|---|---|---|
| III-121 | H | H | (1-ethyl-4-methyl-5-hydroxy-1,2,4-triazol-3(2H)-one) | m.p.: 188° C. |
| III-122 | H | H | (2-)(1-ethyl-4-cyclopropyl-5-cyclopropyl-1,2,4-triazol-3(2H)-one) | |
| III-123 | H | H | (1-ethyl-4-methyl-5-methyl-1,2,4-triazol-3(2H)-one) | m.p.: 131° C. |
| III-124 | (4-) Cl | H | (2-)(1-ethyl-4-methyl-5-CF₃-1,2,4-triazol-3(2H)-one) | m.p.: 109° C. |
| III-125 | (4-) I | H | (2-)(1-ethyl-4-methyl-5-CF₃-1,2,4-triazol-3(2H)-one) | m.p.: 104° C. |
| III-126 | (4-) Br | H | (2-)(1-ethyl-4-methyl-5-CF₃-1,2,4-triazol-3(2H)-one) | m.p.: 99° C. |
| III-127 | (4-) Br | H | (2-)(1-ethyl-4-cyclopropyl-5-cyclopropyl-1,2,4-triazol-3(2H)-one) | m.p.: 174° C. |

TABLE 2-continued

Examples of compounds of the formula (III)

| Ex. No. | (position-) R³ | (position-) (R⁴)ₙ | (position-) -A–Z | physical data |
|---|---|---|---|---|
| III-128 | H | H | (2-) 2-ethyl-4-methyl-5-(methylthio)-2,4-dihydro-3H-1,2,4-triazol-3-one | m.p.: 122° C. |
| III-129 | (4-) Br | H | (2-) 2-ethyl-4-methyl-5-(methylthio)-2,4-dihydro-3H-1,2,4-triazol-3-one | m.p.: 164° C. |
| III-130 | H | H | (2-) 2-ethyl-5-isopropoxy-4-methyl-2,4-dihydro-3H-1,2,4-triazol-3-one | m.p.: 154° C. |
| III-131 | (4-) Br | H | (2-) 2-ethyl-5-isopropoxy-4-methyl-2,4-dihydro-3H-1,2,4-triazol-3-one | m.p.: 161° C. |
| III-132 | (4-) CN | H | (2-) 2-ethyl-4-methyl-5-trifluoromethyl-2,4-dihydro-3H-1,2,4-triazol-3-one | m.p.: 196° C. |
| III-133 | H | H | (2-) 2-ethyl-phthalazin-1(2H)-one | m.p.: 192° C. |
| III-134 | H | H | (2-) 1-ethyl-1H-benzimidazol-2(3H)-one | |

TABLE 2-continued

Examples of compounds of the formula (III)

| Ex. No. | (position-) R³ | (position-) (R⁴)ₙ | (position-) -A–Z | physical data |
|---|---|---|---|---|
| III-135 | (4-) Br | H | (2-) 3-methyl-benzoxazol-2(3H)-one | m.p.: 252° C. |
| III-136 | (2-) NO₂ | (3-) OCH₃ | (4-) 2-ethyl-4-methyl-5-ethoxy-2,4-dihydro-3H-1,2,4-triazol-3-one | logP = 1.65[a)] |
| III-137 | (2-) NO₂ | (3-) OCH₃ | (4-) 2-ethyl-4-methyl-5-methylthio-2,4-dihydro-3H-1,2,4-triazol-3-one | logP = 1.58[a)] |

Starting Materials of the Formula (IV):

Example (IV-1)

Step 1

10 g (49 mmol) of 2-methyl-4-trifluoromethyl-benzoic acid are dissolved in 150 ml of ethanol and admixed with 1 ml of conc. sulphuric acid. The solution is heated under reflux for 24 hours and then concentrated, and the residue is taken up in methylene chloride and extracted with saturated aqueous sodium bicarbonate solution. The methylene chloride phase is dried over sodium sulphate and concentrated under water pump vacuum.

This gives 9 g (80% of theory) of ethyl 2-methyl-4-trifluoromethyl-benzoate as an amorphous residue.

Step 2

9 g (39 mmol) of ethyl 2-methyl-4-trifluoromethyl-benzoate are dissolved in 200 ml of tetrachloromethane and admixed with 7 g (39 mmol) of N-bromo-succinimide and 0.1 g of dibenzoyl peroxide. The mixture is heated under reflux for 6 hours, and the precipitated succinimide is then filtered off and the filtrate is concentrated under water pump vacuum.

This gives 12 g of an amorphous residue which, in addition to ethyl 2-bromomethyl-4-trifluoromethyl-benzoate, contains 17% of ethyl 2,2-dibromomethyl-4-trifluoromethyl-benzoate and 12% of ethyl 2-methyl-4-trifluoromethyl-benzoate.

Step 3

4 g of ethyl 2-bromomethyl-4-trifluoromethyl-benzoate (approximately 70% pure) and 2.28 g (12.8 mmol) of 5-bromo-4-methyl-2,4-dihydro-3H-1,2,4-triazol-3-one are dissolved in 150 ml of acetonitrile, admixed with 5.3 g (38.4 mmol) of potasssium carbonate and heated under reflux with vigoruous stirring for 2 hours. The reaction mixture is taken up in water and extracted repeatedly with methylene chloride. The combined methylene chloride phases are dried over sodium sulphate, concentrated under water pump vacuum and chromatographed.

This gives 2 g (38% of theory) of 5-bromo-4-methyl-2-(2-ethoxycarbonyl-5-trifluoromethyl-benzyl)-2,4-dihydro-3H-1,2,4-triazol-3-one as an amorphous product.

$^1$H-NMR (CDCl$_3$, δ): 5.46 ppm.

Example (IV-2)

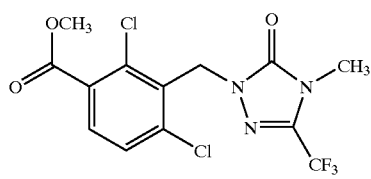

6.7 g (40 mmol) of 4-methyl-5-trifluoromethyl-2,4-dihydro-3H-1,2,4-triazol-3-one are initially charged in 150 ml of acetonitrile and admixed with 11 g (80 mmol) of potassium carbonate. The mixture is heated to 50° C., and a solution of 13.1 g (44 mmol) of methyl 3-bromomethyl-2,4-dichloro-benzoate in 20 ml of acetonitrile is then added dropwise with stirring, and the reaction mixture is heated under reflux with stirring for another 15 hours. The mixture is subsequently concentrated under water pump vacuum, and the residue is taken up in methylene chloride, washed with 1N hydrochloric acid, dried with sodium sulphate and filtered. The filtrate is concentrated under reduced pressure, the residue is digested with petroleum ether and the crystalline product is isolated by filtration with suction.

This gives 14.9 g (97% of theory) of 4-methyl-5-trifluoromethyl-2-(2,6-dichloro-3-methoxycarbonyl-benzyl)-2,4-dihydro-3H-1.2.4-triazol-3-one of melting point 109° C.

By the methods of Examples (IV-1) and (IV-2), it is also possible to prepare, for example, the compounds of the general formula (IVa) listed in Table 3 below.

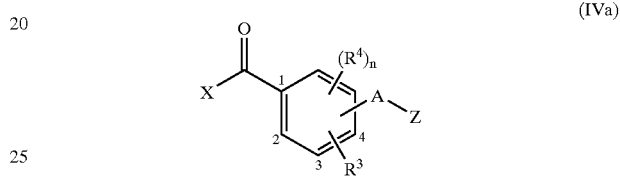

(IVa)

TABLE 3

Examples of compounds of the formula (IV)

| Ex. No. | (position-) R$^3$ | (position-) (R$^4$)$_n$ | (position-) —A—Z | X | physical data |
|---|---|---|---|---|---|
| IV-3 | (2-) Cl | (4-) Cl | (3-) ![structure with N-ethyl, N-CH3, SCH3 triazolone] | OCH$_3$ | m.p.: 229° C. logP = 2.27$^{a)}$ |
| IV-4 | (2-) Cl | (4-) Cl | (3-) ![structure with N-ethyl, N-CH3, OC2H5 triazolone] | OCH$_3$ | m.p.: 120° C. logP = 2.38$^{a)}$ |
| IV-5 | (2-) Cl | (4-) Cl | (3-) ![structure with N-ethyl, N-cyclopropyl, cyclopropyl triazolone] | OCH$_3$ | m.p.: 127° C. logP = 2.55$^{a)}$ |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-6 | (2-) Cl | (4-) Cl | (3-) ethyl-N,N'-triazolone with CH₃ and OCH₃ | OCH₃ | m.p.: 121° C.<br>logP = 2.04[a] |
| IV-7 | (2-) Cl | (4-) Cl | (3-) ethyl-N,N'-triazolone with CH₃ and OC₃H₇-i | OCH₃ | m.p.: 68° C.<br>logP = 2.73[a] |
| IV-8 | (2-) Cl | (4-) Cl | (3-) ethyl-N,N'-triazolone with CH₃ and OCH₂CF₃ | OCH₃ | m.p.: 129° C.<br>logP = 2.72[a] |
| IV-9 | (2-) Cl | (4-) Cl | (3-) ethyl-N,N'-triazolone with CH₃ and Br | OCH₃ | m.p.: 164° C.<br>logP = 2.18[a] |
| IV-10 | (2-) Cl | (4-) Cl | (3-) ethyl-N,N'-triazolone with CH₃ and H | OCH₃ | m.p.: 158° C.<br>logP = 1.55[a] |
| IV-11 | (2-) Cl | (4-) Cl | (3-) ethyl-N,N'-triazolone with CH₃ and cyclopropyl | OCH₃ | m.p.: 106° C.<br>logP = 2.16[a] |
| IV-12 | (2-) Cl | (4-) Cl | (3-) ethyl-N,N'-triazolone with CH₃ and N(CH₃)₂ | OCH₃ | m.p.: 126° C.<br>logP = 2.11[a] |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-13 | (2-) Cl | (4-) Cl | (3-) [1-ethyl-4-methyl-5-methyl-1,2,4-triazol-3(4H)-one] | OCH$_3$ | m.p.: 146° C. logP = 1.65[a] |
| IV-14 | (2-) Cl | (4-) Cl | (3-) [2-ethyl-5,6,7,8-tetrahydro-[1,2,4]triazolo[4,3-a]pyridin-3(2H)-one] | OCH$_3$ | m.p.: 178° C. logP = 1.86[a] |
| IV-15 | (2-) Cl | (4-) Cl | (3-) [1-ethyl-4-cyclopropyl-5-methoxy-1,2,4-triazol-3(4H)-one] | OCH$_3$ | m.p.: 97° C. logP = 2.36[a] |
| IV-16 | (2-) Cl | (4-) Cl | (3-) [1-ethyl-4-cyclopropyl-5-ethoxy-1,2,4-triazol-3(4H)-one] | OCH$_3$ | m.p.: 99° C. logP = 2.73[a] |
| IV-17 | (2-) Cl | (4-) Cl | (3-) [1-ethyl-4-cyclopropyl-5-isopropoxy-1,2,4-triazol-3(4H)-one] | OCH$_3$ | m.p.: 56° C. logP = 3.08[a] |
| IV-18 | (2-) Cl | (4-) Cl | (3-) [1-ethyl-4-cyclopropyl-5-(2,2,2-trifluoroethoxy)-1,2,4-triazol-3(4H)-one] | OCH$_3$ | m.p.: 102° C. logP = 3.05[a] |
| IV-19 | (2-) Cl | (4-) Cl | (3-) [1-ethyl-4-cyclopropyl-5-methylthio-1,2,4-triazol-3(4H)-one] | OCH$_3$ | m.p.: 131° C. logP = 2.70[a] |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-20 | (2-) Cl | (4-) Cl | (3-) *N-ethyl-4-cyclopropyl-5-methyl-1,2,4-triazol-3(4H)-one* | OCH₃ | m.p.: 135° C. logP = 1.97[a] |
| IV-21 | (2-) Cl | (4-) Cl | (3-) *N-ethyl-4-cyclopropyl-5-dimethylamino-1,2,4-triazol-3(4H)-one* | OCH₃ | m.p.: 143° C. logP = 2.42[a] |
| IV-22 | (2-) Cl | (4-) Cl | (3-) *N-ethyl-4-ethoxy-5-ethyl-1,2,4-triazol-3(4H)-one* | OCH₃ | m.p.: 85° C. logP = 2.58[a] |
| IV-23 | (2-) Cl | (4-) Cl | (3-) *1-ethyl-3-methylimidazolidin-2-one* | OCH₃ | logP = 1.98[a] |
| IV-24 | (2-) Cl | (4-) Cl | (3-) *1-ethyl-3-methyltetrahydropyrimidin-2-one* | OCH₃ | logP = 2.07[a] |
| IV-25 | (2-) Cl | (4-) Cl | (3-) *N-ethyl-1,2-benzisothiazol-3(2H)-one-1,1-dioxide* | OCH₃ | m.p.: 157° C. logP = 2.94[a] |
| IV-26 | (4-) CF₃ | H | (2-) *N-ethyl-4-methyl-5-methylsulfonyl-1,2,4-triazol-3(4H)-one* | OC₂H₅ | ¹H NMR (CDCl₃, δ): 5.53 ppm. |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-27 | (4-) NO₂ | H | (3-) 1-ethyl-4-methyl-5-CF₃-1,2,4-triazol-3(4H)-one | OC₂H₅ | ¹H NMR (CDCl₃, δ): 5.48 ppm. |
| IV-28 | (4-) NO₂ | H | (3-) 1-ethyl-4-cyclopropyl-5-cyclopropyl-1,2,4-triazol-3(4H)-one | OC₂H₅ | ¹H NMR (CDCl₃, δ): 5.30 ppm. |
| IV-29 | (4-) SO₂CH₃ | H | (3-) 1-ethyl-4-methyl-5-CF₃-1,2,4-triazol-3(4H)-one | OC₂H₅ | ¹H NMR (CDCl₃, δ): 5.61 ppm. |
| IV-30 | (4-) Cl | H | (3-) 1-ethyl-4-methyl-5-methyl-1,2,4-triazol-3(4H)-one | OC₂H₅ | ¹H NMR (CDCl₃, δ): 5.08 ppm. |
| IV-31 | (4-) Cl | H | (3-) 1-ethyl-4-methyl-5-CF₃-1,2,4-triazol-3(4H)-one | OC₂H₅ | ¹H NMR (CDCl₃, δ): 5.17 ppm. |
| IV-32 | (4-) Cl | H | (3-) 1-ethyl-4-cyclopropyl-5-cyclopropyl-1,2,4-triazol-3(4H)-one | OC₂H₅ | ¹H NMR (CDCl₃, δ): 5.00 ppm. |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-33 | (4-) $SO_2CH_3$ | H | (2-) 1-ethyl-pyrrolidine-2,5-dione | $OC_2H_5$ | logP = 1.53[a] |
| IV-34 | (4-) Br | H | (2-) 2-ethyl-4-ethoxy-5-ethyl-2,4-dihydro-3H-1,2,4-triazol-3-one | $OC_2H_5$ | logP = 3.24[a] |
| IV-35 | (4-) Br | H | (2-) 2-ethyl-4-methyl-5-trifluoromethyl-2,4-dihydro-3H-1,2,4-triazol-3-one | $OC_2H_5$ | logP = 3.40[a] |
| IV-36 | (4-) F | H | (3-) 5-bromo-2-ethyl-4-methyl-2,4-dihydro-3H-1,2,4-triazol-3-one | $OC_2H_5$ | logP = 2.41[a] |
| IV-37 | (4-) F | H | (2-) 2-ethyl-4-methyl-5-methylthio-2,4-dihydro-3H-1,2,4-triazol-3-one | $OC_2H_5$ | logP = 2.45[a] |
| IV-38 | (4-) Br | H | (3-) 2-ethyl-4,5-dimethyl-2,4-dihydro-3H-1,2,4-triazol-3-one | $OC_2H_5$ | logP = 2.06[a] |
| IV-39 | (4-) Br | H | (3-) 5-bromo-2-ethyl-4-methyl-2,4-dihydro-3H-1,2,4-triazol-3-one | $OC_2H_5$ | logP = 2.64[a] |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-40 | (4-) Br | H | (3-) [1-ethyl-4-methyl-5-trifluoromethyl-1,2,4-triazol-3(4H)-one] | $OC_2H_5$ | logP = 3.23[a)] |
| IV-41 | (4-) Br | H | (3-) [1-ethyl-4-cyclopropyl-5-cyclopropyl-1,2,4-triazol-3(4H)-one] | $OC_2H_5$ | logP = 3.02[a)] |
| IV-42 | (4-) Cl | H | (2-) [1-ethyl-4-cyclopropyl-5-ethoxy-1,2,4-triazol-3(4H)-one] | $OC_2H_5$ | logP = 3.23[a)] |
| IV-43 | (4-) Cl | H | (2-) [1-ethyl-4-methyl-5-trifluoromethyl-1,2,4-triazol-3(4H)-one] | $OC_2H_5$ | logP = 3.31[a)] |
| IV-44 | (4-) Cl | H | (2-) [1-ethyl-4-ethoxy-5-ethyl-1,2,4-triazol-3(4H)-one] | $OC_2H_5$ | logP = 3.14[a)] |
| IV-45 | (4-) $NO_2$ | H | (2-) [1-ethyl-4-cyclopropyl-5-ethoxy-1,2,4-triazol-3(4H)-one] | $OC_2H_5$ | logP = 2.42[a)] |
| IV-46 | (4-) $NO_2$ | H | (2-) [1-ethyl-4-methyl-5-methylthio-1,2,4-triazol-3(4H)-one] | $OC_2H_5$ | logP = 2.82[a)] |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-47 | (4-) CF₃ | H | (2-) [1-ethyl-4-cyclopropyl-5-ethoxy-1,2,4-triazol-3(4H)-one] | OC₂H₅ | logP = 3.48[a] |
| IV-48 | (4-) CF₃ | H | (2-) [1-ethyl-4-ethoxy-5-ethyl-1,2,4-triazol-3(4H)-one] | OC₂H₅ | logP = 3.38[a] |
| IV-49 | (4-) CF₃ | H | (2-) [1-ethyl-4-methyl-5-methylthio-1,2,4-triazol-3(4H)-one] | OC₂H₅ | logP = 3.02[a] |
| IV-50 | (4-) CF₃ | H | (2-) [1-ethyl-4-cyclopropyl-5-ethoxy-1,2,4-triazol-3(4H)-one] | OC₃H₇ | logP = 3.91[a] |
| IV-51 | (4-) OCH₃ | H | (2-) [1-ethyl-4-methyl-5-bromo-1,2,4-triazol-3(4H)-one] | OC₂H₅ | |
| IV-52 | (4-) OCH₃ | H | (2-) [1-ethyl-4-ethoxy-5-ethyl-1,2,4-triazol-3(4H)-one] | OC₂H₅ | |
| IV-53 | (4-) CF₃ | H | (2-) [1-ethyl-4-methyl-5-ethoxy-1,2,4-triazol-3(4H)-one] | OC₂H₅ | ¹H NMR (CDCl₃, δ): 5.37 ppm. |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-54 | (4-) CF$_3$ | H | (2-) triazolinone with N-ethyl, N-CH$_3$, OCH$_3$ | OC$_2$H$_5$ | $^1$H NMR (CDCl$_3$, δ): 5.37 ppm. |
| IV-55 | H | H | (2-) triazolinone with N-ethyl, N-CH$_3$, OC$_2$H$_5$ | OC$_2$H$_5$ | |
| IV-56 | H | H | (2-) triazolinone with N-ethyl, N-CH$_3$, OCH$_3$ | OC$_2$H$_5$ | $^1$H NMR (CDCl$_3$, δ): 5.37 ppm. |
| IV-57 | H | H | (2-) triazolinone with N-ethyl, N-OC$_2$H$_5$, C$_2$H$_5$ | OC$_2$H$_5$ | $^1$H NMR (CDCl$_3$, δ): 5.40 ppm. |
| IV-58 | (4-) Br | H | (2-) triazolinone with N-ethyl, N-CH$_3$, OC$_2$H$_5$ | OC$_2$H$_5$ | logP = 2.95$^{a)}$ |
| IV-59 | (4-) Br | H | (2-) triazolinone with N-ethyl, N-CH$_3$, OCH$_3$ | OC$_2$H$_5$ | $^1$H NMR (CDCl$_3$, δ): 5.31 ppm. |
| IV-60 | (4-) Br | H | (2-) N-ethyl succinimide | OC$_2$H$_5$ | logP = 2.44$^{a)}$ |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-61 | (4-) F | H | (2-) 1-ethyl-4-methyl-5-ethoxy-1,2,4-triazol-3(2H)-one | OC₂H₅ | ¹H NMR (CDCl₃, δ): 5.35 ppm. |
| IV-62 | (4-) F | H | (2-) 1-ethyl-4-methyl-5-trifluoromethyl-1,2,4-triazol-3(2H)-one | OC₂H₅ | ¹H NMR (CDCl₃, δ): 5.53 ppm. |
| IV-63 | (4-) F | H | (2-) 1-ethyl-4-ethoxy-5-ethyl-1,2,4-triazol-3(2H)-one | OC₂H₅ | ¹H NMR (CDCl₃, δ): 5.40 ppm. |
| IV-64 | (4-) F | H | (2-) 1-ethyl-4-methyl-5-methoxy-1,2,4-triazol-3(2H)-one | OC₂H₅ | ¹H NMR (CDCl₃, δ): 5.36 ppm. |
| IV-65 | (4-) Br | H | (2-) 1-ethyl-4-methyl-5-isopropoxy-1,2,4-triazol-3(2H)-one | OC₂H₅ | logP = 3.34[a) |
| IV-66 | (4-) Br | H | (2-) 1-ethyl-4-methyl-5-n-propoxy-1,2,4-triazol-3(2H)-one | OC₂H₅ | logP = 3.38[a) |
| IV-67 | (4-) Br | H | (2-) 1-ethyl-4-methyl-5-(2,2,2-trifluoroethoxy)-1,2,4-triazol-3(2H)-one | OC₂H₅ | logP = 3.31[a) |

TABLE 3-continued
Examples of compounds of the formula (IV)
| Ex. No. | (position-) R³ | (position-) (R⁴)ₙ | (position-) —A—Z | X | physical data |
|---|---|---|---|---|---|
| IV-68 | (4-) Br | H | (2-) 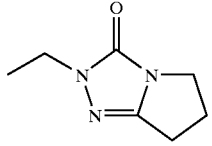 | OC$_2$H$_5$ | logP = 2.16[a)] |
| IV-69 | (4-) Br | H | (2-) 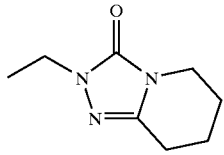 | OC$_2$H$_5$ | logP = 2.41[a)] |
| IV-70 | (4-) CF$_3$ | H | (2-) 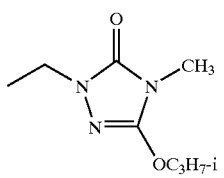 | OC$_2$H$_5$ | logP = 3.51[a)] |
| IV-71 | (4-) CF$_3$ | H | (2-) 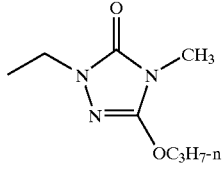 | OC$_2$H$_5$ | logP = 3.54[a)] |
| IV-72 | (4-) Br | H | (2-) 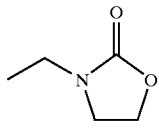 | OC$_2$H$_5$ | logP = 2.36[a)] |
| IV-73 | (4-) Br | H | (2-) 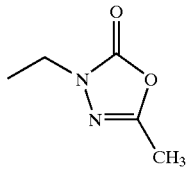 | OC$_2$H$_5$ | logP = 2.88[a)] |
| IV-74 | (4-) CF$_3$ | H | (2-) 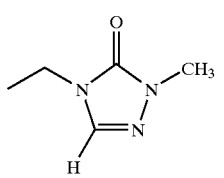 | OC$_2$H$_5$ | logP = 2.68[a)] |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-75 | (4-) Br | H | (2-) triazolinone with N-ethyl, N-CH₃, Br | $OC_2H_5$ | logP = 2.80[a] |
| IV-76 | (4-) CF₃ | H | (3-) triazolinone with N-ethyl, N-cyclopropyl, OCH₃ | $OC_2H_5$ | logP = 3.87[a] |
| IV-77 | (4-) CF₃ | H | (2-) triazolinone with N-ethyl, N-cyclopropyl, CH₂OCH₃ | $OC_2H_5$ | logP = 2.88[a] |
| IV-78 | (4-) CF₃ | H | (2-) triazolinone with N-ethyl, N-CH₃, CH₂OCH₃ | $OC_2H_5$ | logP = 2.60[a] |
| IV-79 | (4-) CF₃ | H | (2-) triazolinone with N-ethyl, N-cyclopropyl, Br | $OC_2H_5$ | logP = 3.35[a] |
| IV-80 | (4-) Br | H | (2-) triazolinone with N-ethyl, N-CH₃, SCH₃ | $OC_2H_5$ | logP = 2.86[a] |
| IV-81 | (4-) Cl | H | (2-) triazolinone with N-ethyl, N-CH₃, SCH₃ | $OC_2H_5$ | logP = 2.83[a] |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-82 | (4-) Br | H | (2-) triazolinone with N-ethyl, N-CH₃, N(CH₃)₂ substituents | OC₂H₅ | logP = 2.60[a] |
| IV-83 | (4-) CF₃ | H | (2-) triazolinone with N-ethyl, N-C₂H₅, OC₂H₅ substituents | OC₂H₅ | ¹H NMR (CDCl₃, δ): 5.36 ppm. |
| IV-84 | (4-) CF₃ | H | (2-) triazolinone with N-ethyl, N-C₂H₅, OCH₃ substituents | OC₂H₅ | ¹H NMR (CDCl₃, δ): 5.37 ppm. |
| IV-85 | (4-) CF₃ | H | (2-) triazolinone with N-ethyl, N-CH₃, N(CH₃)₂ substituents | OC₂H₅ | logP = 2.79[a] |
| IV-86 | (4-) CF₃ | H | (2-) benzisothiazol-3(2H)-one 1,1-dioxide N-ethyl (saccharin) | OC₂H₅ | logP = 3.67[a] |
| IV-87 | (4-) CF₃ | H | (2-) N-ethylphthalimide | OC₂H₅ | logP = 3.80[a] |
| IV-88 | (3-) CH₃ | H | (2-) triazolinone with N-ethyl, N-CH₃, OC₂H₅ substituents | OC₂H₅ | logP = 2.54[a] |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-89 | (4-) SO₂CH₃ | H | (2-) 1-ethyl-4-methyl-5-(methylthio)-1,2,4-triazol-3(4H)-one | OC₂H₅ | logP = 1.82[a] |
| IV-90 | (4-) CF₃ | H | (2-) 1-ethyl-5-(trifluoromethyl)pyrimidine-2,4(1H,3H)-dione | OC₂H₅ | logP = 2.93[a] |
| IV-91 | (4-) CF₃ | H | (2-) 4-cyclopropyl-1-ethyl-5-methoxy-1,2,4-triazol-3(4H)-one | OC₂H₅ | logP = 3.08[a] |
| IV-92 | (4-) CF₃ | H | (2-) 3-ethyl-5-methyl-1,3,4-oxadiazol-2(3H)-one | OC₂H₅ | logP = 3.04[a] |
| IV-93 | (4-) CF₃ | H | (2-) 1-ethyl-4-methyl-5-(2,2,2-trifluoroethoxy)-1,2,4-triazol-3(4H)-one | OC₂H₅ | logP = 3.45[a] |
| IV-94 | (4-) F | H | (2-) 5-(dimethylamino)-1-ethyl-4-methyl-1,2,4-triazol-3(4H)-one | OC₂H₅ | logP = 2.21[a] |
| IV-95 | (4-) F | H | (2-) 1-ethyl-4-methyl-5-(n-propoxy)-1,2,4-triazol-3(4H)-one | OC₂H₅ | logP = 2.96[a] |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-96 | (4-) F | H | (2-) 2-ethyl-4-methyl-5-(methoxymethyl)-triazolinone | $OC_2H_5$ | logP = 2.05[a) |
| IV-97 | (4-) F | H | (2-) 2-ethyl-4-cyclopropyl-5-methoxy-triazolinone | $OC_2H_5$ | logP = 2.50[a) |
| IV-98 | (4-) F | H | (2-) 2-ethyl-4-cyclopropyl-5-ethoxy-triazolinone | $OC_2H_5$ | logP = 2.89[a) |
| IV-99 | (4-) CF₃ | H | (2-) 2-ethyl-4,4-dimethyl-5-methyl-pyrazolinone | $OC_2H_5$ | logP = 2.91[a) |
| IV-100 | (4-) Cl | H | (2-) 2-ethyl-4-methyl-5-methyl-triazolinone | $OC_2H_5$ | ¹H NMR (CDCl₃, δ): 5.39 ppm. |
| IV-101 | (4-) Cl | H | (2-) 2-ethyl-4-methyl-5-trifluoromethyl-triazolinone | $OC_2H_5$ | ¹H NMR (CDCl₃, δ): 5.50 ppm. |
| IV-102 | (4-) Cl | H | (2-) 2-ethyl-4-methyl-5-methanesulfonyl-triazolinone | $OC_2H_5$ | ¹H NMR (CDCl₃, δ): 5.49 ppm. |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-103 | (4-) CF₃ | H | (2-) triazolinone with N-ethyl, N-CH₃, CH₃ | OC₂H₅ | ¹H NMR (CDCl₃, δ): 5.29 ppm. |
| IV-104 | (4-) CF₃ | H | (2-) triazolinone with N-ethyl, N-CH₃, CF₃ | OC₂H₅ | ¹H NMR (CDCl₃, δ): 5.53 ppm. |
| IV-105 | (4-) CF₃ | H | (2-) triazolinone with N-ethyl, N-cyclopropyl, cyclopropyl | OC₂H₅ | ¹H NMR (CDCl₃, δ): 5.34 ppm. |
| IV-106 | (4-) SO₂CH₃ | H | (2-) triazolinone with N-ethyl, N-cyclopropyl, cyclopropyl | OC₂H₅ | ¹H NMR (CDCl₃, δ): 5.39 ppm. |
| IV-107 | (4-) SO₂CH₃ | H | (2-) triazolinone with N-ethyl, N-CH₃, CH₃ | OC₂H₅ | ¹H NMR (CDCl₃, δ): 5.43 ppm. |
| IV-108 | (4-) SO₂CH₃ | H | (2-) triazolinone with N-ethyl, N-CH₃, N(CH₃)₂ | OC₂H₅ | ¹H NMR (CDCl₃, δ): 5.40 ppm. |

TABLE 3-continued

Examples of compounds of the formula (IV)

| Ex. No. | (position-) R³ | (position-) (R⁴)ₙ | (position-) —A—Z | X | physical data |
|---|---|---|---|---|---|
| IV-109 | (4-) SO₂CH₃ | H | (2-) 1-ethyl-4-methyl-5-ethoxy-1,2,4-triazol-3(2H)-one | OC₂H₅ | ¹H NMR (CDCl₃, δ): 5.38 ppm. |
| IV-110 | (4-) Br | H | (2-) 1-ethyl-4-methyl-5-trifluoromethyl-1,2,4-triazol-3(2H)-one | OC₂H₅ | ¹H NMR (CDCl₃, δ): 5.49 ppm. |
| IV-111 | H | H | (2-) 1-ethyl-4-cyclopropyl-5-cyclopropyl-1,2,4-triazol-3(2H)-one | OC₂H₅ | ¹H NMR (CDCl₃, δ): 5.3 ppm. |
| IV-112 | H | H | (2-) 1-ethyl-4-methyl-5-methylthio-1,2,4-triazol-3(2H)-one | OC₂H₅ | ¹H NMR (CDCl₃, δ): 5.44 ppm. |
| IV-113 | (4-) CF₃ | H | (2-) 1-ethyl-4-methyl-2-methyl-1,2,4-triazolidine-3,5-dione | OC₂H₅ | logP = 2.58 [a)] |
| IV-114 | (4-) SO₂CH₃ | H | (2-) 1-ethyl-4-methyl-5-methylthio-1,2,4-triazol-3(2H)-one | OCH₃ | logP = 1.53 [a)] |
| IV-115 | (4-) SO₂CH₃ | H | (2-) 1-ethyl-4-methyl-5-ethoxy-1,2,4-triazol-3(2H)-one | OCH₃ | logP = 1.59 [a)] |

TABLE 3-continued

Examples of compounds of the formula (IV)

| Ex. No. | (position-) $R^3$ | (position-) $(R^4)_n$ | (position-) —A—Z | X | physical data |
|---|---|---|---|---|---|
| IV-116 | (4-) I | H | (2-) triazolinone with ethyl, CH₃, OC₂H₅ | OCH₃ | logP = 2.68[a] |
| IV-117 | (4-) CF₃ | H | (2-) triazolinone with ethyl, CH₃, OC₂H₅ | OCH₃ | logP = 2.74[a] |
| IV-118 | (4-) CF₃ | H | (2-) triazolinone with ethyl, CH₃, SCH₃ | OCH₃ | logP = 2.65[a] |
| IV-119 | (4-) CF₃ | H | (2-) triazolinone with ethyl, CH₃, Br | OC₂H₅ | logP = 2.96[a] |
| IV-120 | H | H | (2-) triazolidinedione with ethyl, CH₃, H₃C | OCH₃ | m.p.: 106° C. |
| IV-121 | (2-) NO₂ | (3-) OCH₃ | (4-) triazolinone with ethyl, CH₃, OC₂H₅ | OCH₃ | logP = 2.27[a] |
| IV-122 | (2-) NO₂ | (3-) OCH₃ | (4-) triazolinone with ethyl, CH₃, SCH₃ | OCH₃ | logP = 2.19[a] |

The logP values given in the Tables were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in the Tables are labelled [a].

(b) Mobile phases for the determination in the neutral range: 0.01-molar aqueous phosphate buffer solution, acetonitrile; linear gradient from 10% acetonitrile to 90% acetonitrile—the corresponding data in the Tables are labelled [b].

Calibration was carried out using unbranched alkan-2-ones (having 3 to 16 carbon atoms) whose logP values are known (determination of the logP values using the retention times by linear interpolation between two successive alkanones).

The lambda-max values were determined using the UV spectra from 200 nm to 400 nm in the maxima of the chromatographic signals.

ration of active compound such that the particular amount of active compound desired is applied per unit area. The concentration of the spray liquor is chosen so that the particular amount of active compound desired is applied in 1000 liters of water per hectare.

After three weeks, the degree of damage to the plants is assesssed in % damage in comparison to the development of the untreated control.

The figures denote:

| | |
|---|---|
| 0% = | no effect (like untreated control) |
| 100% = | total destruction |

In this test, for example the compounds of Preparation Example 1 and 10 exhibit strong activity against weeds, and some of them are tolerated well by crop plants, such as, for example, maize.

TABLE A

Pre-emergence test/greenhouse

| Active compound of Preparation Example No. | Amount used (g ai./ha) | Maize | Cyperus | Abutilon |
|---|---|---|---|---|
| (1) | 1000 | — | 100 | 100 |
| (10) | 500 | 0 | 100 | 90 |

Use Examples

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is sprayed with the prepa- Example B Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way that the particular amounts of active compound desired are applied per unit area. The concentration of the spray liquor is chosen so that the particular amounts of active compound desired are applied in 1000 l of water/ha.

After three weeks, the degree of damage to the plants is assessed in % damage in comparison to the development of the untreated control.

The figures denote:

| |
|---|
| 0% = no effect (like untreated control) |
| 100% = total destruction |

In this test, for example the compounds of Preparation Example 10 and 15 exhibit strong activity against weeds, and some of them are tolerated well by crop plants, such as, for example, maize.

TABLE B

Post emergence test/greenhouse

| Active compound of Preparation Example No. | Amount used (g ai./ha) | Maize | Amaranthus | Sinapis |
|---|---|---|---|---|
| 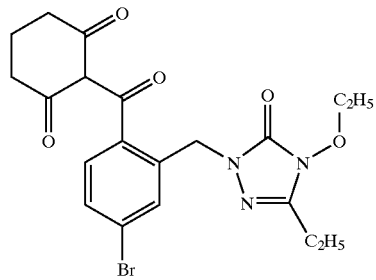 (10) | 500 | 20 | 95 | 80 |
| 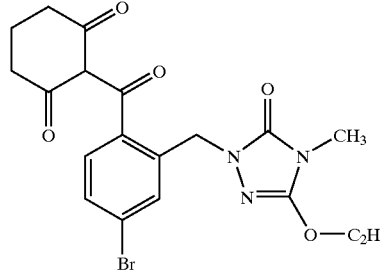 (15) | 1000 | 0 | 90 | 80 |

What is claimed is:

1. A substituted benzoylcyclohexanedione of the formula (I),

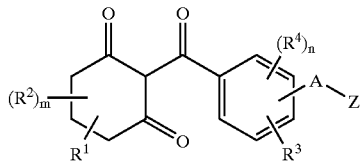

in which m represents the numbers 0, 1, 2 or 3, n represents the numbers 0, 1, 2 or 3, A represents a single bond or represents alkanediyl (alkylene), $R^1$ represents hydrogen or represents unsubstituted or substituted alkyl or alkoxycarbonyl, $R^2$ represents unsubstituted or substituted alkyl, or together with $R^1$ represents alkanediyl (alkylene) where in this case m represents 1 and $R^1$ and $R^2$ are located at the same carbon atom ("geminal") or at two adjacent carbon atoms ("vicinal"), $R^3$ represents hydrogen, nitro, cyano, carboxyl, carbamoyl, thiocarbamoyl, halogen, or represents unsubstituted or substituted alkyl, alkoxy, alkylthio, alkylsulphinyl, alkylsulphonyl, alkylamino, dialkylamino or dialkylaminosulphonyl, $R^4$ represents nitro, cyano, carboxyl, carbamoyl, thiocarbamoyl, halogen, or represents unsubstituted or substituted alkyl, alkoxy, alkylthio, alkylsulphinyl, alkylsulphonyl, alkylamino, dialkylamino or dialkylaminosulphonyl, and Z represents one of the heterocyclic groupings below

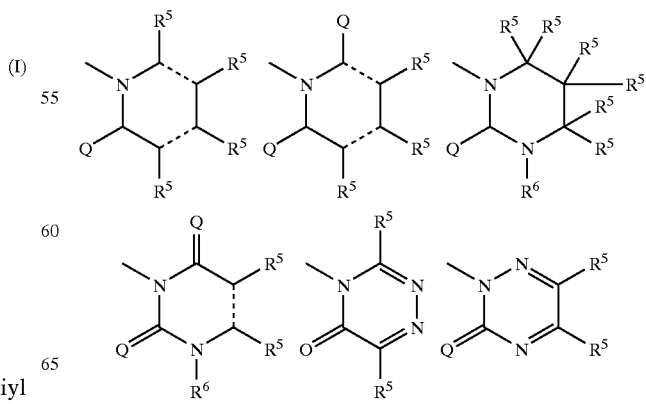

137

-continued

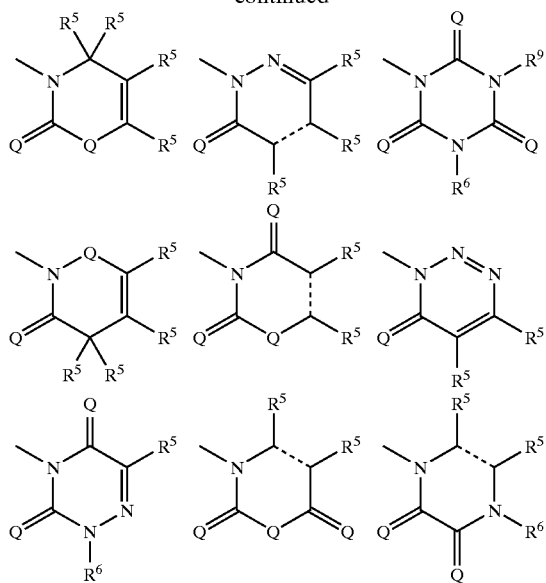

in which the bond drawn broken in each case denotes a single bond or a double bond, Q represents oxygen, $R^5$ represents hydrogen, hydroxyl, mercapto, cyano, halogen, or represents unsubstituted or halogen-, $C_1$–$C_4$-alkoxy-, $C_1$–$C_4$-alkylthio-, $C_1$–$C_4$-alkylsulphinyl-or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, or represents unsubstituted or halogen-substituted alkylamino or dialkylamino having in each case up to 6 carbon atoms in the alkyl groups, or represents unsubstituted or halogen-substituted alkenyl, alkinyl, alkenyloxy, alkenylthio or alkenylamino having in each case up to 6 carbon atoms in the alkenyl or alkinyl groups, or represents unsubstituted or halogen-substituted cycloalkyl, cycloalkylalkyl, cycloalkyloxy, cycloalkylthio or cycloalkylamino having in each case 3 to 6 carbon atoms in the cycloalkyl groups and optionally up to 4 carbon atoms in the alkyl moiety, or represents unsubstituted or halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, and $R^6$ represents hydrogen, hydroxyl, amino, alkylideneamino having up to 4 carbon atoms, or represents unsubstituted or halogen- or $C_1$–$C_4$-alkoxy-substituted alkyl, alkoxy, alkylamino, dialkylamino or alkanoylamino having in each case up to 6 carbon atoms in the alkyl groups, or represents unsubstituted or halogen-substituted alkenyl, alkinyl or alkenyloxy having in each case up to 6 carbon atoms in the alkenyl or alkinyl groups, or represents unsubstituted or halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents unsubstituted or halogen-, $C_1$–$C_4$-alkyl- or $C_1$–$C_4$-alkoxy-substituted phenyl or benzyl, or together with an adjacent radical $R^5$ or $R^6$ represents unsubstituted or halogen- or $C_1$–$C_4$-alkyl-substituted alkanediyl having 3 to 5 carbon atoms, or—in the case that two adjacent radicals $R^5$ and $R^5$ are located at a double bond—together with the adjacent radical $R^5$ also represents a benzo grouping including all possible tautomeric forms of the substituted benzoylcyclohexanedione of the formula (I) and the possible salts of the substituted benzoylcyclohexanedione of the formula (I).

2. A substituted benzoylcyclohexanedione according to claim 1, wherein:

m represents the numbers 0, 1 or 2, n represents the numbers 0, 1 or 2,

A represents alkanediyl (alkylene) having 1 to 4 carbon atoms, $R^1$ represents a single bond or represents hydrogen, or represents unsubstituted or halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms or represents alkoxycarbonyl having up to 6 carbon atoms, $R^2$ represents unsubstituted or halogen-substituted alkyl having 1 to 6 carbon atoms, or together with $R^1$ represents alkanediyl (alkylene) having 2 to 5 carbon atoms, where in this case m represents 1 and $R^1$ and $R^2$ are located at the same carbon atom ("geminal") or at two adjacent carbon atoms ("vicinal"), $R^3$ represents hydrogen, nitro, cyano, carboxyl, carbamoyl, thiocarbamoyl, halogen, represents unsubstituted or halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having up to 4 carbon atoms in the alkyl groups, or represents alkylamino, dialkylamino or dialkylaminosulphonyl having up to 4 carbon atoms in the alkyl groups, $R^4$ represents nitro, cyano, carboxyl, carbamoyl, thiocarbamoyl, halogen, represents unsubstituted or halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having up to 4 carbon atoms in the alkyl groups, or represents alkylamino, dialkylamino or dialkylaminosulphonyl having up to 4 carbon atoms in the alkyl groups, and Z represents one of the heterocyclic groupings below

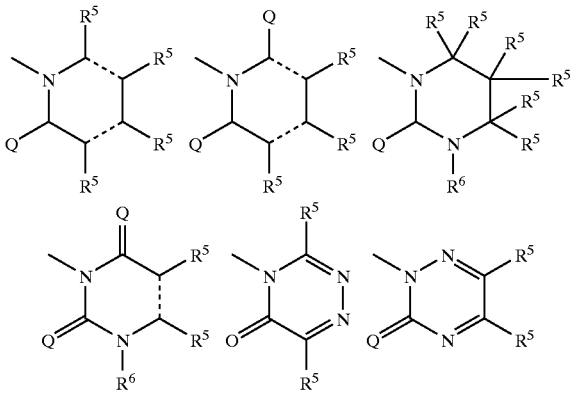

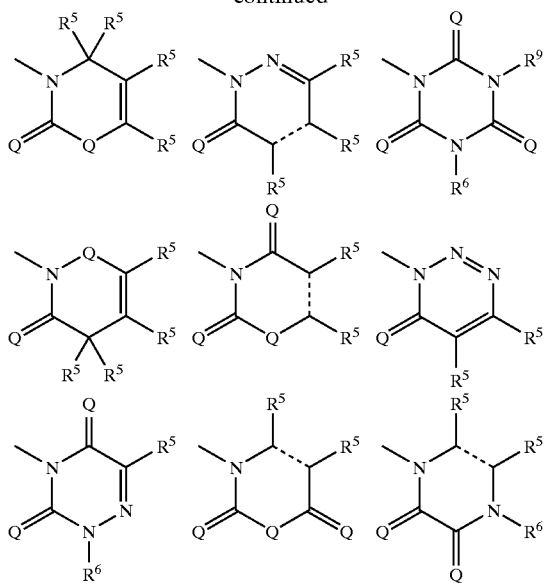

in which the bond drawn broken in each case denotes a single bond or a double bond, Q represents oxygen, R⁵ represents hydrogen, hydroxyl, mercapto, cyano, halogen, or represents unsubstituted or halogen-, $C_1$–$C_4$-alkoxy-, $C_1$–$C_4$-alkylthio-, $C_1$–$C_4$-alkylsulphinyl-or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, or represents unsubstituted or halogen-substituted alkylamino or dialkylamino having in each case up to 6 carbon atoms in the alkyl groups, or represents unsubstituted or halogen-substituted alkenyl, alkinyl, alkenyloxy, alkenylthio or alkenylamino having in each case up to 6 carbon atoms in the alkenyl or alkinyl groups, or represents unsubstituted or halogen-substituted cycloalkyl, cycloalkylalkyl, cycloalkyloxy, cycloalkylthio or cycloalkylamino having in each case 3 to 6 carbon atoms in the cycloalkyl groups and optionally up to 4 carbon atoms in the alkyl moiety, or represents unsubstituted or -halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, and R⁶ represents hydrogen, hydroxyl, amino, alkylideneamino having up to 4 carbon atoms, or represents unsubstituted or halogen- or $C_1$–$C_4$-alkoxy-substituted alkyl, alkoxy, alkylamino, dialkylamino or alkanoylamino having in each case up to 6 carbon atoms in the alkyl groups, or represents unsubstituted or halogen-substituted alkenyl, alkinyl or alkenyloxy having in each case up to 6 carbon atoms in the alkenyl or alkinyl groups, or represents unsubstituted or halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents unsubstituted or halogen-, $C_1$–$C_4$-alkyl- or $C_1$–$C_4$-alkoxy-substituted phenyl or benzyl, or together with an adjacent radical R⁵ or R⁶ represents unsubstituted or halogen- or $C_1$–$C_4$-alkyl-substituted alkanediyl having 3 to 5 carbon atoms, or—in the case that two adjacent radicals R⁵ and R⁵ are located at a double bond—together with the adjacent radical R⁵ also represents a benzo grouping.

3. Substituted benzoylcyclohexanediones according to claim 1, wherein:

m represents the numbers 0, 1 or 2, n represents the numbers 0, 1 or 2,

A represents a single bond, methylene, ethylidene (ethane-1, 1-diyl) or dimethylene (ethane-1,2-diyl), R¹ represents hydrogen, or represents unsubstituted or fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i- or s-butyl, or represents methoxycarbonyl, ethoxycarbonyl, n- or i-propoxycarbonyl, R² represents methyl, ethyl, n- or i-propyl, or together with R¹ represents methylene, ethane-1,1-diyl (ethylidene, —CH(CH₃)—), ethane-1,2-diyl (dimethylene, —CH₂CH₂—), propane-1,3-diyl (trimethylene, —CH₂CH₂CH₂—), butane-1,4-diyl (tetramethylene, —CH₂CH₂CH₂CH₂—) or pentane-1, 5-diyl (pentamethylene, —CH₂CH₂CH₂CH₂CH₂—), where in this case m represents 1 and R¹ and R² are located at the same carbon atom ("geminal") or at two adjacent carbon atoms ("vicinal"), R³ represents hydrogen, nitro, cyano, carboxyl, carbamoyl, thiocarbamoyl, fluorine, chlorine, bromine, or represents unsubstituted or fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethyl-sulphonyl-substituted methyl, ethyl, n- or i-propyl, n-, i-, s- or t-butyl, or represents unsubstituted or fluorine- and/or chlorine-, methoxy-, ethoxy-, n- or i-propoxy-substituted methoxy, ethoxy, n- or i-propoxy, or represents unsubstituted or fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, R⁴ represents nitro, cyano, carboxyl, carbamoyl, thiocarbamoyl, fluorine, chlorine, bromine, or represents unsubstituted or fluorine-, chlorine-, fluorine and chlorine-, methoxy-, ethoxy-, n- or i-propoxy-, methylthio-, ethylthio-, -n- or i-propylthio-, methylsulphinyl-, ethylsulphinyl-, methylsulphonyl- or ethylsulphonyl-substituted methyl, ethyl, n- or i-propyl, n-, i-, s- or t-butyl, or represents unsubstituted or fluorine-, chlorine-, fluorine and chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, and Z represents one of the heterocyclic groupings below

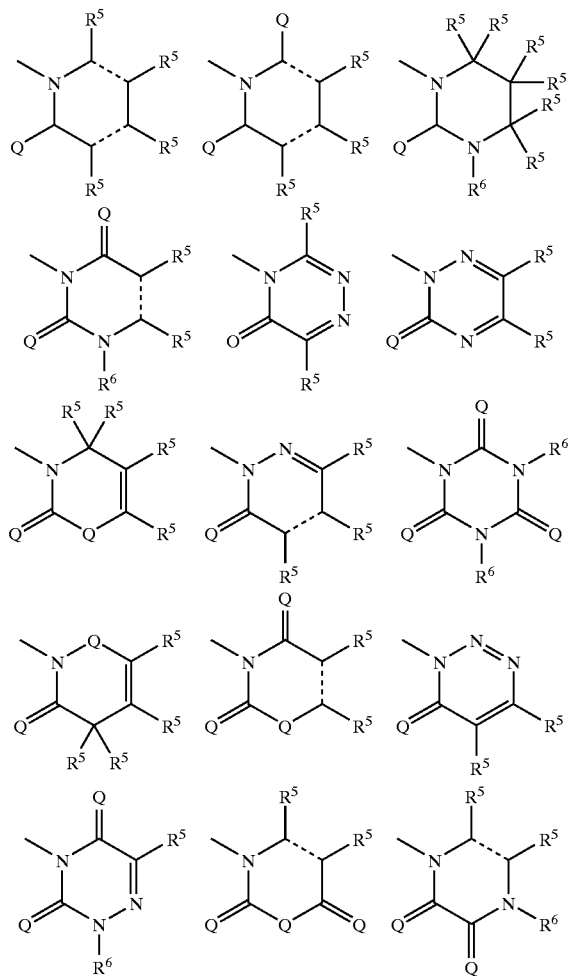

in which the bond drawn broken in each case denotes a single bond or a double bond, Q represents oxygen, $R^5$ represents hydrogen, hydroxyl, mercapto, cyano, fluorine, chlorine, bromine, iodine, or represents unsubstituted or fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, or represents unsubstituted or fluorine-, chlorine-, or fluorine and chlorine-substituted ethenyl, propenyl, butenenyl, ethinyl, propinyl, butinyl, propenyloxy, butenyloxy, propenylthio, butenylthio, propenylamino or butenylamino, or represents unsubstituted or fluorine-, chlorine-, or fluorine and chlorine-substituted cyclopropyl, cyclobutyl, cyclopentyl, cyclohexyl, cyclopropylmethyl, cyclobutylmethyl, cyclopentylmethyl, cyclohexylmethyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents unsubstitued or fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, and $R^6$ represents hydrogen, hydroxyl, amino, or represents unsubstituted or fluorine-, chlorine-, or fluorine and chlorine-, methoxy-, or ethoxy-substituted methyl, ethyl, n- or i-propyl, n-, i- or s-butyl, methoxy, ethoxy, n- or i-propoxy, methylamino, ethylamino or dimethylamino, or represents unsubstituted or fluorine-, chlorine-, or fluorine and chlorine-substituted ethenyl, propenyl, ethinyl, propinyl or propenyloxy, or represents unsubstituted or fluorine-, chlorine-, or fluorine and chlorine-substituted cyclopropyl, cyclobutyl, cyclopentyl, cyclohexyl, cyclopropylmethyl, cyclobutylmethyl, cyclopentylmethyl, cyclohexylmethyl, or represents unsubstituted or fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents unsubstituted or methyl- and/or ethyl-substituted propane-1,3-diyl (trimethylene) or butane-1,4-diyl (tetramethylene), or—in the case that two adjacent radicals $R^5$ and $R^5$ are located at a double bond—together with the adjacent radical $R^5$ also represents a benzo grouping.

4. A method of controlling undesirable plants, comprising the step of applying one or more substituted benzoylcyclohexanediones according to claim 1 to undesirable plants or their habitats.

5. A herbicidal composition comprising one or more substituted benzoylcyclohexanediones according to claim 1 and an extender.

* * * * *